(12) United States Patent
Lebel et al.

(10) Patent No.: US 7,361,806 B2
(45) Date of Patent: Apr. 22, 2008

(54) TRANSGENIC PLANTS EXPRESSING A CELLULASE

(75) Inventors: Edouard G Lebel, Therwil (CH); Peter B Heifetz, San Diego, CA (US); Eric R Ward, Durham, NC (US); Scott J Uknes, Apex, NC (US)

(73) Assignee: Syngenta Participations AG (CH)

( * ) Notice: Subject to any disclaimer, the term of this patent is extended or adjusted under 35 U.S.C. 154(b) by 0 days.

(21) Appl. No.: 09/901,737

(22) Filed: Jul. 9, 2001

(65) Prior Publication Data

US 2002/0062502 A1 May 23, 2002

Related U.S. Application Data

(62) Division of application No. 09/254,780, filed as application No. PCT/US97/16187 on Sep. 12, 1997, now abandoned.

(60) Provisional application No. 60/054,528, filed on Aug. 4, 1997, provisional application No. 60/025,985, filed on Sep. 12, 1996.

(51) Int. Cl.
*C12N 15/82* (2006.01)
(52) U.S. Cl. .................... 800/288; 800/284
(58) Field of Classification Search ............ 800/298
See application file for complete search history.

(56) References Cited

U.S. PATENT DOCUMENTS

| | | | | |
|---|---|---|---|---|
| 4,904,599 | A | 2/1990 | Ozaki ................ | 435/252.33 |
| 5,168,064 | A * | 12/1992 | Bennett et al. ............ | 435/209 |
| 5,393,670 | A | 2/1995 | Knowles ............... | 435/252.33 |
| 5,457,046 | A | 10/1995 | Woldike ............... | 435/209 |
| 5,470,725 | A * | 11/1995 | Borriss et al. ............ | 435/105 |
| 5,475,101 | A | 12/1995 | Ward .................. | 536/23.74 |
| 5,536,655 | A | 7/1996 | Thomas et al. ........... | 435/209 |
| 5,543,576 | A | 8/1996 | van Ooijen et al. | |
| 5,545,818 | A | 8/1996 | McBride et al. .......... | 800/205 |
| 5,614,395 | A * | 3/1997 | Ryals et al. .............. | 435/4 |
| 5,705,375 | A | 1/1998 | Van Ooyen et al. | |
| 5,925,806 | A | 7/1999 | McBride et al. .......... | 800/298 |
| 5,981,835 | A | 11/1999 | Austin-Phillips et al. ... | 800/278 |
| 6,277,615 | B1 | 8/2001 | Varghese et al. | |
| 6,818,803 | B1 | 11/2004 | Austin-Phillips et al. | |
| 7,102,057 | B2 | 9/2006 | Lanahan et al. | |

FOREIGN PATENT DOCUMENTS

| EP | 0332104 | 9/1989 |
|---|---|---|
| EP | 0449376 | 2/1991 |
| EP | 0479359 | 8/1992 |
| EP | 0589841 | 3/1994 |
| WO | 9116440 | 10/1991 |
| WO | 9201042 | 1/1992 |
| WO | 9520668 | 3/1995 |
| WO | 9514099 | 5/1995 |
| WO | 9516783 | 6/1995 |
| WO | 9525787 | 9/1995 |
| WO | 9604781 | 2/1996 |

OTHER PUBLICATIONS

Lashbrook et al., Two Divergent Endo-B-1, 4-glucanase Gene Exhibit Overlapping Expression in Ripening Fruit and Abscising Flowers, Oct. 1994, The Plant Cell, vol. 6, pp. 1485-1493.*
Yoshikawa et al., Resistance to Fungal Disease in Transgenic Tobacco Plants Expressing the . . . , 1993, Naturwissenschaften, vol. 80, pp. 417-420.*
Lao et al., DNA Sequence of Three B-1, 4-Endoglucanase Gene from *Thermomonospora fusca*, Jun. 1991, Journal of Bacteriology, vol. 173, No. 11, pp. 3397-3407.*
Takeuchi et al., Molecular Cloning and Ethylene Induction of mRNA Encoding a Phytoalexin . . . , 1990, Plant Physiol, vol. 93, pp. 673-682.*
Melchers et al., Extracellular targeting of the vacuolar tabacco proteins AP24, chitinase and B-1, 3-glucanase in transgenic plants, 1993, Plant Molecular Biology, vol. 21, pp. 583-593.*
http://kr.expasy.org/cgi-bin/enzyme-search-de, 2004.*
http://kr.expasy.org/cgi-bin/nicezyme.pl?3.2.1.4, 2004.*
http://kr.expasy.org/enzyme, 2004.*
GenBank Accession No. M73321, 1998.*
Aspegren, et al., *Secretion of a heat stable fungal beta-glucanase from transgenic suspension-cultured barley cells Molecular Breeding*, vol. 1 (1995) pp. 91-99.
Hausmann, R., "The T7 Group." in ed. Calendar, Richard, *The Bacteriophages* (New York and London, Plenum Press, 1988), pp. 259-289.
Heifetz, et al., *Chemical Regulation of nuclear and plastid transgenes in plants*, Supplement to Plant Physiology, vol. 114(3) (Jul. 1997) pp. 308.
Kotani, et al., *Nucleotide sequence and expression of the cloned gene of bacteriophage SP6 RNA polymerase Nucleic Acids Research*, vol. 15 (1987) pp. 2653-2664.
McBride, et al., *Controlled expression of plastid transgenes in plants based on a nuclear DNA-encoded and plastid-targeted T7 RNA polymerase Proceedings of the National Academy of Science of USA*, vol. 91 (Jul. 1994) pp. 7301-7305.
McGraw, et al., *Sequence and analysis of the gene for bacteriophage T3 RNA polymerase Nucleic Acids Research*, vol. 13 (1985) pp. 6753-6766.
Pen, et al., *Production of Active Bacillus Licheniformis Alpha-Amylase in Tobacco and its Application Bio/Technology*, vol. 10(3) (Mar. 1992) pp. 292-296.
Herbers, K., et al. *A thermostable xylanase from Clostridium thermocellum expressed at high levels in the apoplast of transgenic tobacco has no detrimental effects and is easily purified, Bio/technology* vol. 13:63-66 (Jan. 1995).

(Continued)

*Primary Examiner*—Anne R Kubelik
(74) *Attorney, Agent, or Firm*—Karen Moon Bruce

(57) ABSTRACT

The instant disclosure describes the application of genetic engineering techniques to produce cellulase in plants. Cellulase coding sequences operably linked to promoters active in plants may be transformed into the nuclear genome and/or the plastid genome of a plant. As cellulases may be toxic to plants, chemically-inducible or wound-inducible promoters may be employed. Additionally, the expressed cellulases may be targeted to vacuoles or other cellular organelles.

28 Claims, 2 Drawing Sheets

OTHER PUBLICATIONS

Collmer, A. and Wilson, D.B., *Cloning and Expression of a Thermomonospora YX Endocellulase Gene in E. coli Bio/Technology*, (Sep. 1983), pp. 594-601.

Ghangas, G.S. and Wilson, D.B., *Cloning of the Thermomonospora fusca Endoglucanase E2 Gene in Streptomyces lividans: Affinity Purification and Functional Domains of the Cloned Gene Product Applied and Environmental Microbiology*, vol. 54, No. 10 (Oct. 1988), pp. 2521-2526.

Jung et al, *DNA Sequences and Expression in Streptomyces lividans of an Exoglucanase Gene and an Endoglucanase Gene from Thermomonospora fusca Applied and Environmental Microbiology*, vol. 59, No. 9 (Sep. 1993), pp. 3032-3043.

Lao et al, *DNA Sequences of Three β-1, 4-Endoglucanase Genes from Thermomonospora fusca Journal of Bacteriology*, vol. 173, No. 11 (Jun. 1991), pp. 3397-3407.

Thomas et al, "Initial Approaches to Artificial Cellulase Systems for Conversion of Biomas to Ethanol", in Saddler, J.N.; Penner, M.H., eds. *Enzymatic Degradation of Insoluble Polysaccharides*, ACS Series 618, Washington, DC: American Chemical Society; pp. 208-236.

Wilson, D.B., *Biochemistry and Genetics of Actinomycete Cellulases Critical Reviews in Biotechnology*, vol. 12(1/2) (1992), pp. 45-63.

Lashbrook et al., *Functional Analysis of Cx-Cellulase (Endo β-1-4-Glucanase) Gene Expression in Transgenic Tomato Fruit, Cellular and Molecular Aspects of the Plant Hormone Ethylene*, J.C. Pech et al. (eds.) (Kluwer Academic Publishers), (1993), pp. 123-128.

Koehler, et al., *The Gene Promoter for a Bean Abscission Cellulase is Ethylene-Induced in Transgenic Tomato and Shows High Sequence Conservation with a Soybean Abscission Cellulase, Plant Molecular Biology*, 31: 595-606.

Kawazu, et al., *Expression of a Ruminococcus Albus Cellulase Gene in Tobacco Suspension Cells, Journal of Fermentation and Bioengineering* 82(3): 205-209.

B. Henrissat et al., *Cellulase families revealed by hydrophobic cluster analysis, Gene*, 81(1989):83-95.

N. R. Gilkes et al., *Domains in Microbial β-1,4-Glycanases: Sequence Conservation, Function, and Enzyme Families, Microbiological Reviews*, Jun. 1991, p. 303-315.

Gilbert, "Production and characterization of cellulases and xylanses from the thermophilic ascomycete Thielavis Terrestris 255b", Univ. Microfilms Int., Order No. DANN93618 (1992) pp. 243.

Goodenough et al., "Protein Engineering to change thermal stability for food enzymes", Biochem Soc Trans. Aug. 19 (3): 655-62.

Goodenough et al., "A Review of Protein Engineering for the Food Industry", Mol. Biotechnol., Oct. 4(2) 151-66.

Romaniec et al., "Molecular Cloning of Clostridium Thermocellum DNA and the expression of Further Novel AEndo-b-1-4-glucanase Genes in *Escherichia coli*", Journal of General Microbiology (1987) 133; 1297-1307.

Collings, et al., "Endo-B1-1-4-glucanase, exo-B-1, 4-glucanese, B-glucosidase and related enzyme activity in culture filtrates of thermophilic, thermotolerant and mesophilic filamentous fungi", 131 Microbios 56 131-147 1988.

Spezio et al., "Crystal Structure of the Catalytic domain of a Thermophilic Endocellulase", Biochemistry (1993) 32, 9906-9916.

Juy et al., "Three-dimensional structure of a thermostable bacterial cellulase", Cellul. Hydrolysis Ferment., Proc. CEC Workshop (1992) 18-29.

Presutti et al., "Cloning of Three Endoglucanase Genes From Thermomonospore Curvate Into *Escherichia coli*", Journal of Biotechnology, 17 (1991) 177-188.

Jin et al., "Purification and Characterization of Cellulases from Clostridium Thermocopriae sp. nov. JT3-3", Journal of Fermentation and Bioengineering vol. 67, No. 1, 8-13 (1989).

Kvesitadze et al., "Thermostable Endo-B-1,4-glucanase adn endo-b-1,4-xylanase activity in culture filtrates and a purified enzyme fraction in the thermophillic fungus *Allescheria terrestris*", Microbios 80(323) 115-123 (1994).

Matsumura et al., "Cumulative Effect of Intragenci Amino-Aid Replacements on the Thermostability of a Protein", Nature, vol. 323 25 (Sep. 1, 1986) pp. 356-358.

Baker et al., "A New Thermostable Endoglucanase, Acidothermus Cellulolyticus E1 Synergism with *Trichoderma reesei* CBH1 and comparison to *Thermomonospora fusca* E5" Applied Biochemistry and Biotechnology (1994) 45-46, 245-56.

Politz et al., "Determinants for the Enhanced Thermostability of Hybrid (1-3, 1-4)-Beta-glucanases", Eur. J. Biochem. 216 829-834 (1993).

Lao et al., "DNA Sequences of Three Beta-1,4-Endoglucanase Genes from *Thermomonospora fusca*" Journal of Bacteriology, (Jun. 1991) p. 3397-3407.

Robson et al., "Cellulases of Bacterial Origin" Enzyme Microb. Technol. (1989) vol. 11, October, pp. 626-644.

Sakon et al., Crystal Structure of Thermostable Family 5 Endocellulase E1 From Acidothermus Cellulolyticus in Complex With Cellotetraose Biochemistry (1996) 35, 10648-10660.

Davies et al., "Crystallization and Preliminary X-Ray Analysis of a Fungal Endoglucanase I", J. Mol. Biol. (1992) 226, 970-972.

Chilarra et al., "Multiple Crystal Forms of Endoglucanase CeID: Signal Peptide Residues Modulate Lattice Formation", J. Mol. Biol. (111995) 248,225-232.

Dominguez et al., "Characterization of Two Crystals Forms of Clostridium Thermocellum Endogiocanase CeIC", PROTEINS: Structure, Function, and Genetics 19:158-160 (1994).

Arnold, "Engineering Proteins for Nonnatural Environments", FASEB J. (Jun. 1993) vol. 7 pp. 744-749.

Nosoh et al., "Protein Engineering for Thermostability" Trends Biotechnol. (Jan. 1990) 8 (1) pp. 16-20.

Imanaka et al., "A New Way of Enhancing the Thermostability of Proteases" Nature vol. 324 18/25 (Dec. 1988) pp. 695-697.

Matthews et al, "Enhanced Protein Thermostability From Site-Directed Mutations That Decrease the Entropy of Unfolding" Biochemistry vol. 84 pp. 6663-6667 (October 9187).

Arias, "Engineering Protein Thermal Stability Sequence Statistics Point to Residue Substitutions in a-Helices" J. Mol. Biol. (1989) 206, pp. 397-4406.

Davies et al., "Structure and Function of Endoglucanase V" Nature vol. 365 ; Sep. 23, 1993, pp. 362-364.

\* cited by examiner

TRANSGENIC PLANTS EXPRESSING A CELLULASE

CROSS REFERENCE TO RELATED APPLICATIONS

This application is a divisional of U.S. Application Ser. No. 09/254,780, filed Mar. 10, 1999 now abandoned, which is a national stage application under 35 U.S.C. § 371 of International Application No. PCT/US97/16187, filed Sep. 12, 1997, which claims the benefit of U.S. Provisional Application Ser. No. 60/054,528, filed Aug. 4, 1997, and U.S. Provisional Application Ser. No. 60/025,985, filed Sep. 12, 1996, all of which are herein incorporated by reference in their entireties.

FIELD OF THE INVENTION

The invention relates to the control of gene expression in transgenic plastids and to transgenic plants capable of expressing cellulose-degrading enzymes.

BACKGROUND OF THE INVENTION

Industrial Uses for Cellulose-Degrading Enzymes

1. Converting Biomass to Ethanol

The production of ethanol has received considerable attention over the years as an octane booster, fuel extender, or neat liquid fuel. For example, in Brazil, up to 90% of new cars run on neat ethanol, whereas the remainder run on an ethanol/gasoline blend. In the United States, about 7% of all gasoline sold currently contains ethanol, usually a blend of 90% gasoline:10% ethanol. Fuel ethanol is currently produced primarily from sugar cane in Brazil; however, in the United States, sugar prices are typically too high to make sugarcane attractive as a feedstock for ethanol production. In the United States, fuel ethanol is currently produced primarily from corn and other starch-rich grains. However, the production of one billion gallons of ethanol per year corresponds to 400 million bushels of corn per year, which means that the existing corn ethanol industry is insufficient to supply the current fuel market. In addition, corn ethanol is currently too expensive to cost-effectively compete with gasoline. To make a significant impact on the transportation fuel market, ethanol needs a broader and cheaper resource base than industry currently has at its disposal. Technology for utilizing cellulosic biomass, for example wood, grass, and waste biomass from various commercial processes, as a feedstock could expand the resource base to accommodate most of the fuel market needs in the United States, because cellulosic biomass is cheap and plentiful.

The major components of terrestrial plants are two families of sugar polymers, cellulose and hemicellulose. Cellulose fibers comprise 4%-50% of the total dry weight of stems, roots, and leaves. These fibers are embedded in a matrix of hemicellulose and phenolic polymers. Cellulose is a polymer composed of six-carbon sugars, mostly glucose, linked by β-1,4 linkages. Hemicellulose is a polymer of sugars, but the types of sugars vary with the source of biomass. With the exception of softwoods, the five-carbon sugar xylose is the predominant component in hemicellulose.

While all ethanol production ultimately involves fermentation processes from sugars, the technology for ethanol production from cellulosic biomass is fundamentally different from ethanol production from starchy food crops. While both require hydrolysis of the feedstock (starch or cellulose) into fermentable sugars, starch is easier to hydrolyze and enzymes that degrade starch, amylases, are relatively inexpensive. In contrast, cellulose degrading enzymes or "cellulases" are currently less effective and more expensive. Hydrolysis of cellulosic biomass to fermentable sugars can also occur though acid hydrolysis processes, which will not be discussed in detail. Cellulases are a family of enzymes that work in concert to break down cellulose to its simple sugar components under much milder conditions compared to acid hydrolysis. In addition, these enzymes catalyze highly specific reactions and are required in much smaller quantities compared to acid hydrolysis reactions.

Hydrolysis of cellulose and starch produces glucose by the following reaction:

$$n\ C_6H_{10}O_5 + n\ H_2O \rightarrow n\ C_6H_{12}O_6$$

After glucose is formed, fermentation thereof to ethanol proceeds by the following reaction:

$$C_6H_{12}O_6 \rightarrow 2\ CO_2 + 2\ C_2H_5OH$$

For lignocellulosic biomass such as hardwoods, the hemicellulosic fraction must also be considered. For biomass predominantly containing the five-carbon sugar xylose in the hemicellulose, the hydrolysis reaction proceeds as follows:

$$n\ C_5H_8O_4 + n\ H_2O \rightarrow n\ C_5H_{10}O_5$$

whereas the xylose produced is fermented to ethanol with the following stoichiometry:

$$3\ C_5H_{10}O_5 \rightarrow 5\ CO_2 + 5\ C_2H_5OH$$

2. Other Potential Uses for Cellulose-Degrading Enzymes

In addition to use in converting biomass to ethanol, cellulases have potential utility in other industrial processes, such as any industrial process that depends on a supply of fermentable sugars. Cellulases also have potential utility in the pulp and paper industry and in the textile industry to reduce the current dependency on acid hydrolysis, which is a major cause of water pollution.

In the animal feed industry, cellulases have utility as a feed additive to aid the digestion of cellulosic material. Silage, for example, can be made more digesible by the addition of cellulases or plants which express cellulases.

Characteristics of Cellulose-Degrading Enzymes

As stated above, cellulose and hemicellulose are the principal sources of fermentable sugars in lignocellulosic feedstocks; however, nature has designed woody tissue for effective resistance to microbial attack. A wide variety of organisms including bacteria and fungi possess cellulolytic activity. To be effective, cellulose-degrading microorganisms typically produce cellulase enzyme systems characterized by multiple enzymatic activities that work synergistically to reduce cellulose to cellobiose, and then to glucose. At least three different enzymatic activities are required to accomplish this task. β-1,4-endoglucanases (EC 3.2.1.4, also called endocellulases) cleave β1,4-glycosidic linkages randomly along the cellulose chain. β-1,4-exoglucanases (EC 3.2.1.91, also called cellobiohydrolases, CBH) cleave cellobiose from either the reducing or the non-reducing end of a cellulose chain. 1,4-β-D-glucosidases (EC 3.2.1.21, also called cellobioses) hydrolyze aryl- and alkyl-β-D-glucosides.

Filamentous fungi are well known as a resource for industrial cellulases. However, this resource is generally regarded as too expensive for large scale industrial ethanol production. Some of the most prolific producers of extracellular cellulases are various strains of *Trichoderma reesei*. By contrast, cellulases are typically produced by celluloytic bacteria such as *Thermomonospora fusca* at much lower level than by filamentous fungi. However, cellulases from *T. fusca* and other bacteria have been shown to have very high specific activities over a broad pH range and also have the desirable property of thermal stability. The *T. fusca* genes that encode cellulose-degrading enzymes have been cloned and extensively characterized. (See, e.g., Collmer et al. (1983) Bio/Technology 1:594-601, hereby incorporated by reference; Ghangas et al. (1988) Appl. Environ. Microbiol. 54:2521-2526, hereby incorporated by reference; and Wilson (1992) Crit. Rev. Biotechnol. 12:45-63, hereby incorporated by reference). In addition, the DNA sequences of a cellobiohydrolase gene and an endoglucanase gene from *T. fusca* have been determined (Jung et al. (1993) Appl. Environ. Microbiol. 59:3032-3043, hereby incorporated by reference); and the DNA sequences of three endoglucanase genes from *T. fusca* have also been determined (Lao et al. (1991) J. Bacteriol. 173:3397-3407, hereby incorporated by reference).

Efforts are currently being undertaken to utilize recombinant cellulase-producing bacterial or fungal hosts to produce various cellulases for use in biomass-to-ethanol processes. Candidate cellulases to be used in such recombinant systems are selected based on factors such as kinetics, temperature and pH tolerance, resistance to end product inhibition, and their synergistic effects. (See, for example, Thomas et al., "Initial Approaches to Artificial Cellulase Systems for Conversion of Biomass to Ethanol"; *Enzymatic Degradation of Insoluble Carbohydrates*, J. N. Saddler and M. H. Penner, eds., ACS Symposium Series 618:208-36, 1995, American Chemical Society, Washington, D.C., hereby incorporated by reference in its entirety). Examples of heterologous expression of endoglucanases, exoglucanases, and β-D-glucosidases in *E. coli, Bacillus subtilis*, and *Streptomyces lividans* have been reported (Lejeune et al., *Biosynthesis and Biodegradation of Cellulose*; Haigler, C. H.; Weimer, P. J., Eds.; Marcel Dekker: New York, N.Y., 1990; pp. 623-671). In addition, the expression of a *B. subtilis* endoglucanase and a *C. fimi* β-D-glucosidase in *E. coli* has been demonstrated (Yoo et al. (1992) Biotechnol. Lett. 14:77-82).

While there is ongoing research to develop a multiple-gene expression system in a suitable host that produces high levels of endoglucanase, exoglucanase, and β-D-glucosidase activities in optimal proportions for the degradation of cellulosic biomass, the end result of this research will be simply be an improved bioreactor for producing large quantities of highly active cellulases for use in conventional biomass-to-ethanol processes as well as other industrial applications. Thus, this research is limited by the conventional problems inherent with all such fermentation processes, including the fact that biomass is naturally resistant to external enzymatic attack.

Current approaches to this problem are limited to using recombinant hosts that will not themselves be harmed by their genetically-engineered production of cellulose-degrading enzymes. For example, it would be expected that only hosts that do not themselves include cellulose would be suitable for use in such bioreactors. Plants, therefore, would not be expected to be suitable hosts for recombinant cellulase genes. Transforming a plant to produce high levels of cellulase is counterintuitive and presents special technical difficulties. To overcome these difficulties, it was necessary to develop new expression systems, allowing for very high levels of expression, preferably under tight regulation to prevent damage to the plant during its development. These novel expression systems would also have applications beyond cellulase production.

SUMMARY OF THE INVENTION

In a first embodiment, the present invention addresses the need for a plentiful, inexpensive source of cellulose-degrading enzymes for such industries as the fuel ethanol production industry, cattle feed industry, and the paper and textile industries. Accordingly, the present invention provides for the production of cellulose-degrading enzymes in plants via the application of genetic engineering techniques. Higher plants make promising candidates for use as in vivo bioreactors for cellulase production. They have high biomass yields, production is easily scaled up and does not require aseptic conditions, and complex post-translational modification of plant-synthesized proteins is commonplace. Moreover, levels of transgene-encoded proteins in plants may exceed 1% of total protein content. However, as plants depend on cellulose for structural integrity, it would be expected that cellulose-degrading enzymes would be toxic to plants. Accordingly, cellulase genes represent an ideal target for technology relating to the chemical induction of gene expression and the targeting of gene products to cell storage structures.

In the present invention, cellulase coding sequences are fused to promoters active in plants and transformed into the nuclear genome or the plastid genome. Cellulases that may be expressed in plants according to the present invention include, but are not limited to, endoglucanases, exoglucanases, and β-D-glucosidases, preferably derived from non-plant sources such as microorganisms (e.g. bacteria or fungi). A preferred promoter is the chemically-inducible tobacco PR-1a promoter; however, in certain situations, constitutive promoters such as the CaMV 35S promoter may be used as well. With a chemically inducible promoter, expression of the cellulase genes transformed into plants may be activated at an appropriate time by foliar application of a chemical inducer.

Where plastid transformation is used, vectors are suitably constructed using a phage promoter, such as the phage T7 gene 10 promoter, the transcriptional activation of which is dependent upon an RNA polymerase such as the phage T7 RNA polymerase. In one case, plastid transformation vectors containing a phage promoter fused to a cellulase gene are transformed into the chloroplast genome. The resulting line is crossed to a transgenic line containing a nuclear coding region for a phage RNA polymerase supplemented with a chloroplast-targeting sequence and operably linked to a constitutive promoter such as the CAMV 35S promoter, resulting in constitutive cellulase expression in the chloroplasts of plants resulting from this cross. Chloroplast expression has the advantage that the cellulase is less damaging to the plastid as it contains little or no cellulose.

In addition to using chemically-inducible promoters, the expressed cellulases may be targeted to certain organelles such as vacuoles to alleviate toxicity problems. For vacuole-targeted expression of cellulases, plants are transfonned with vectors that include a vacuolar targeting sequence such as that from a tobacco chitinase gene. In this case, the expressed cellulases will be stored in the vacuoles where they will not be able to degrade cellulose and harm the plant.

The invention thus provides:

A plant which expresses a cellulose-degrading enzyme, e.g. a cellulose degrading enzyme not naturally expressed in plants, for example a plant comprising a heterologous DNA sequence coding for a cellulose degrading enzyme stably integrated into its nuclear or plastid DNA, preferably under control of an inducible promoter, e.g., a wound-inducible or chemically-inducible promoter, for example either operably linked to the inducible promoter or under control of transactivator-regulated promoter wherein the corresponding transactivator is under control of the inducible promoter;

also including the seed for such a plant, which seed is optionally treated (e.g., primed or coated) and/or packaged, e.g. placed in a bag with instructions for use.

The invention further provides:

A method for producing a cellulose-degrading enzyme comprising cultivating a cellulase-expressing plant;

a method for producing ethanol comprising fermenting a cellulase-expressing plant; and a method for enhancing the digestibility of animal feed, e.g., silage, comprising adding a cellulase-expressing plant to the feed mix.

These methods may further comprise enhancing cellulose degradation by combining two or more different cellulose degrading enzymes, e.g., enzymes acting at different stages in the cellulose biodegradation pathway, e.g., in synergistically active combination, either by expressing said enzymes in a single plant or by combining two or more plants each expressing a different cellulose degrading enzyme.

The invention further provides:

A plant expressible expression cassette comprising a coding region for a cellulose-degrading enzyme, preferably under control of an inducible promoter, e.g., a wound inducible or chemically inducible promoter; for example a plastid expressible expression cassette comprising a promoter, e.g., a transactivator-mediated promoter regulated by a nuclear transactivator (e.g., the T7 promoter when the transactivator is T7 RNA polymerase the expression of which is optionally under control of an inducible promoter), and operably linked to coding region for a cellulose-degrading enzyme;

a vector comprising such a plant expressible expression cassette; and a plant transformed with such a vector, or a transgenic plant which comprises in its genome, e.g., its plasstid genome, such a plant expressible expression cassette.

In a further embodiment, the present invention encompasses a novel system of plastid expression, wherein the gene expressed in the plastid is under control of a transactivator-regulated promoter, and the gene for the transactivator is in the nuclear DNA, under control of an inducible promoter. For example, plastid transformation vectors are typically constructed using a phage promoter, such as the phage T7 gene 10 promoter, the transcriptional activation of which is dependent upon an RNA polymerase such as the phage T7 RNA polymerase. The resulting line is crossed to a transgenic line containing a nuclear coding region for a phage RNA polymerase supplemented with a chloroplast-targeting sequence and operably linked to a chemically inducible promoter such as the tobacco PR-1a promoter. Expression of the gene of interest in the chloroplasts of plants resulting from this cross is then activated by foliar application of a chemical inducer. The novel, inducible transactivator-mediated plastid expression system described herein is shown to be tightly regulatable, with no detectable expression prior to induction and exceptionally high expression and accumulation of protein following induction.

The invention thus additionally provides:

A plant expressible expression cassette comprising an inducible promoter, e.g., a wound-inducible or chemically-inducible promoter, for example the tobacco PR-1a promoter, operably linked to a DNA sequence coding for a transactivator (preferably a transactivator not naturally occurring in plants, preferably a RNA polymerase or DNA binding protein, e.g., T7 RNA polymerase), said transactivator being fused to a plastid targeting sequence, e.g., a chloroplast targeting sequence;

a vector comprising such a plant expressible cassette; and a plant transformed with such a vector or a transgenic plant the genome of which comprises such a plant expressible expression cassette.

The invention furthermore provides:

A plant comprising a heterologous nuclear expression cassette comprising an inducible promoter, e.g., a wound-inducible or chemically-inducible promoter, for example the tobacco PR-1a promoter, operably linked to a DNA sequence coding for a transactivator (preferably a transactivator not naturally occurring in plants, preferably a RNA polymerase or DNA binding protein, e.g., T7 RNA polymerase), said transactivator being optionally fused to a plastid targeting sequence, e.g., a chloroplast targeting sequence (e.g., a plant expressible expression cassette as described above); and a heterologous plastid expression cassette comprising a transactivator-mediated promoter regulated by the transactivator (e.g., the T7 promoter when the transactivator is T7 RNA polymerase) and operably linked to a DNA sequence of interest, e.g., coding for a protein of interest (e.g., an enzyme, a carbohydrate degrading enzyme, for example GUS or a cellulose-degrading enzyme) or for a functional RNA of interest (e.g., antisense RNA);

also including the seed for such a plant, which seed is optionally treated (e.g., primed or coated) and/or packaged, e.g. placed in a bag or other container with instructions for use.

The invention also comprises:

A method of producing a plant as described above comprising pollinating a plant comprising a heterologous plastid expression cassette comprising a transactivator-mediated promoter regulated and operably linked to a DNA sequence coding for a protein of interest with pollen from a plant comprising a heterologous nuclear expression cassette comprising an inducible promoter operably linked to a DNA sequence coding for a transactivator capable of regulating said transactivator-mediated promoter;

recovering seed from the plant thus pollinated; and cultivating a plant as described above from said seed.

DEFINITIONS

"Cellulose-degrading enzymes" are described herein and include cellulases, cellobiohydrolases, cellobioses and other enzymes involved in breaking down cellulose and hemicellulose into simple sugars such as glucose and xylose. Preferably, the cellulose-degrading enzyme used in the present invention are of non-plant origin, e.g., of microbial origin, preferably of bacterial origin, for example from a bacteria of the genus *Thermomonospora*, e.g., from *T. fusca*.

"Expression cassette" as used herein means a DNA sequence capable of directing expression of a gene in plant cells, comprising a promoter operably linked to a coding region of interest which is operably linked to a termination region. The coding region usually codes for a protein of interest but may also code for a functional RNA of interest, for example antisense RNA or a nontranslated RNA that, in the sense or antisense direction, inhibits expression of a particular gene, e.g., antisense RNA. The gene may be chimeric, meaning that at least one component of the gene is heterologous with respect to at least one other component of the gene. The gene may also be one which is naturally occurring but has been obtained in a recombinant form useful for genetic transformation of a plant. Typically, however, the expression cassette is heterologous with respect to the host, i.e., the particular DNA sequence of the expression cassette does not occur naturally in the host cell and must have been introduced into the host cell or an ancestor of the host cell by a transformation event. A "nuclear expression cassette" is an expression cassette which is integrated into the nuclear DNA of the host. A "plastid expression cassette" is an expression cassette which is integrated into the plastid DNA of the host. A plastid expression cassette as described herein may optionally comprise a polycistronic operon containing two or more cistronic coding sequences of interest under control of a single promoter, e.g., a transactivator-mediated promoter, e.g., wherein one of the coding sequences of interest encodes an antisense mRNA which inhibits expression of clpP or other plastid protease, thereby enhancing accumulation of protein expressed the the other coding sequence or sequences of interest.

"Heterologous" as used herein means "of different natural origin". For example, if a plant is transformed with a gene derived from another organism, particularly from another species, that gene is heterologous with respect to that plant and also with respect to descendants of the plant which carry that gene.

"Homoplastidic" refers to a plant, plant tissue or plant cell wherein all of the plastids are genetically identical. This is the normal state in a plant when the plastids have not been transformed, mutated, or otherwise genetically altered. In different tissues or stages of development, the plastids may take different forms, e.g., chloroplasts, proplastids, etioplasts, amyloplasts, chromoplasts, and so forth.

An "inducible promoter" is a promoter which initiates transcription only when the plant is exposed to some particular external stimulus, as distinguished from constitutive promoters or promoters specific to a specific tissue or organ or stage of development. Particularly preferred for the present invention are chemically-inducible promoters and wound-inducible promoters. Chemically inducible promoters include plant-derived promoters, such as the promoters in the systemic acquired resistance pathway, for example the PR promoters, e.g., the PR-1, PR-2, PR-3, PR-4, and PR-5 promoters, especially the tobacco PR-1a promoter and the *Arabidopsis* PR-1 promoter, which initiate transcription when the plant is exposed to BTH and related chemicals. See U.S. Pat. No. 5,614,395, incorporated herein by reference, and U.S. Provisional Application No. 60/027,228, incorporated herein by reference. Chemically-inducible promoters also include receptor-mediated systems, e.g., those derived from other organisms, such as steroid-dependent gene expression, copper-dependent gene expression, tetracycline-dependent gene expression, and particularly the expression system utilizing the USP receptor from *Drosophila* mediated by juvenile growth hormone and its agonists, described in PCT/EP96/04224, incorporated herein by reference, as well as systems utilizing combinations of receptors, e.g., as described in PCT/EP96/00686, incorporated herein by reference. Wound inducible promoters include promoters for proteinase inhibitors, e.g., the proteinase inhibitor II promoter from potato, and other plant-derived promoters involved in the wound response pathway, such as promoters for polyphenyl oxidases, LAP and TD. See generally, C. Gatz, "Chemical Control of Gene Expression", Annu. Rev. Plant Physiol. Plant Mol. Biol. (1997) 48: 89-108, the contents of which are incorporated herein by reference.

A "plant" refers to any plant or part of a plant at any stage of development. In some embodiments of the invention, the plants may be lethally wounded to induce expression or may be induced to express lethal levels of a desired protein, and so the term "plant" as used herein is specifically intended to encompass plants and plant material which have been seriously damaged or killed, as well as viable plants, cuttings, cell or tissue cultures, and seeds.

A "transactivator" is a protein which, by itself or in combination with one or more additional proteins, is capable of causing transcription of a coding region under control of a corresponding transactivator-mediated promoter. Examples of transactivator systems include phage T7 gene 10 promoter, the transcriptional activation of which is dependent upon a specific RNA polymerase such as the phage T7 RNA polymerase. The transactivator is typically an RNA polymerase or DNA binding protein capable of interacting with a particular promoter to initiate transcription, either by activating the promoter directly or by inactivating a repressor gene, e.g., by suppressing expression or accumulation of a repressor protein. The DNA binding protein may be a chimeric protein comprising a binding region (e.g., the GAL4 binding region) linked to an appropriate transcriptional activator domain. Some transactivator systems may have multiple transactivators, for example promoters which require not only a polymerase but also a specific subunit (sigma factor) for promotor recognition, DNA binding, or transcriptional activation. The transactivator is preferably heterologous with respect to the plant.

DETAILED DESCRIPTION OF THE INVENTION

Figure 1:
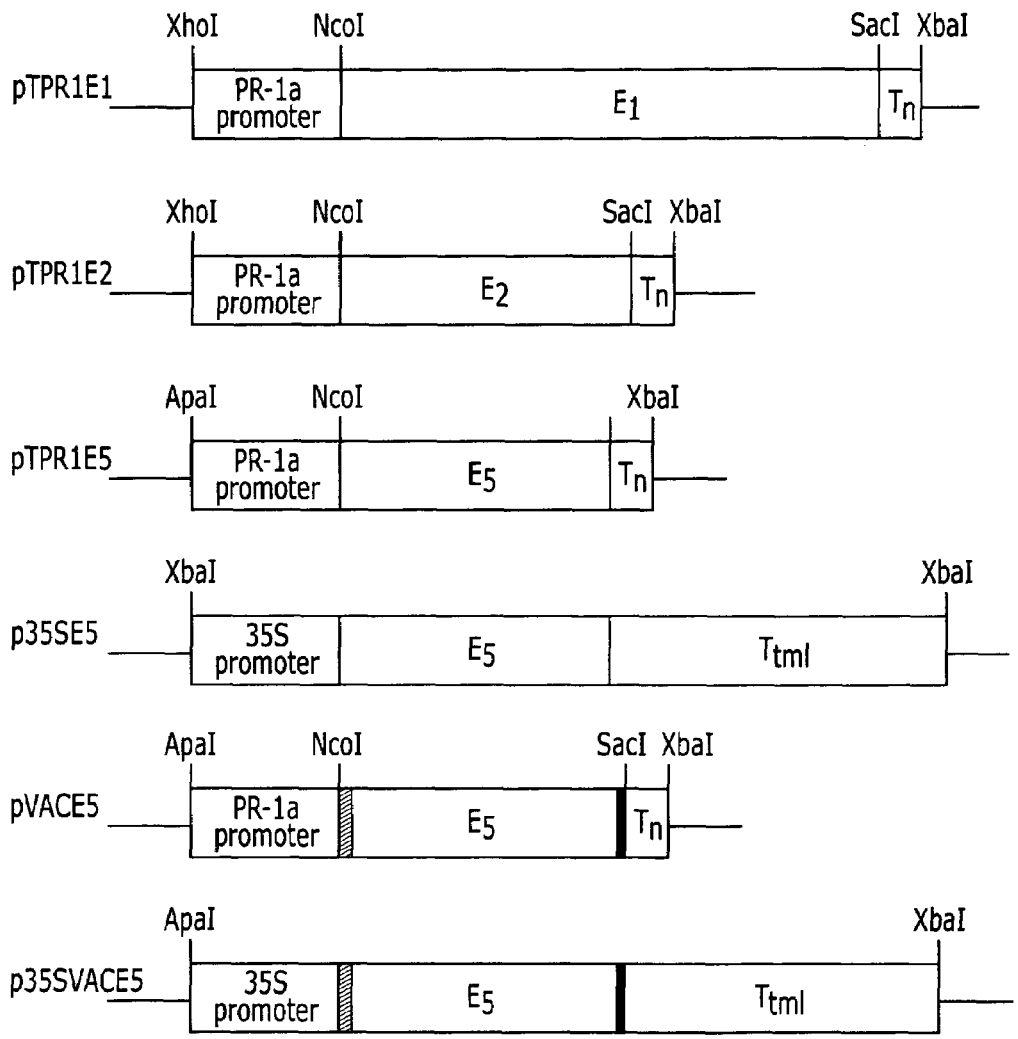
FIG. 1 is a schematic description of chimeric gene constructs described in the Examples for cellulase expression in plants. Hatched boxes represent the E5 gene signal sequence and closed boxes represent the vacuolar targeting sequence from a tobacco chitinase gene. $T_n$ codes for nos termination sequences and Ttml for tml termination sequences.

The present invention addresses the need for a plentiful, inexpensive source of cellulose-degrading enzymes for such industries as the fuel ethanol production industry, cattle feed industry, and the paper and textile industries by replacing the conventional industrial cellulases produced by fungi with cellulases produced in plants. By genetically engineering plants to produce their own cellulases, external application of cellulases for cellulose degradation will be unnecessary. For example, lignocellulosic biomass destined to become ethanol could serve as its own source of cellulase by utilizing the present invention. In fact, transgenic plants according to the present invention would not necessarily have to comprise all of the feedstock in a bioreactor; rather, they could be used in conjunction with non-transformed cellulosic feedstock, whereby the cellulases produced by the transgenic plants would degrade the cellulose of all the feedstock, including the non-transgenic feedstock. Cellulose degradation processes using transgenic biomass produced according to the present invention can be carried out more inexpensively, easily, and more environmentally safe than can conventional methods.

The feedstock could be any type of lignocelluosic material such as high-biomass plants grown specifically for use as a source of biomass or waste portions of plants grown primarily for other purposes, such as stems and leaves of crop plants. Plants transformed with cellulase genes may be transformed with constructs that provide constitutive expression of cellulases if the particular plants can survive their own production of cellulases. If a particular type of plant experiences undue toxicity problems from the constitutive expression of cellulases, then the plant is preferably transformed with constructs that allow cellulase production only when desired. For example, with chemically inducible cellulase constructs, one chemically induces cellulase expression just before harvesting plants so that just as the plants are being killed by their own production of cellulases, they are harvested anyway. Plant tissue is then crushed, ground, or chopped to release the cellulases then added to a bioreactor in which the lignocellulosic biomass would be degraded into simple sugars by the action of the cellulases expressed in the transgenic plants.

The chimeric genes constructed according to the present invention may be transformed into any suitable plant tissue. As used in conjunction with the present invention, the term "plant tissue" includes, but is not limited to, whole plants, plant cells, plant organs, plant seeds, protoplasts, callus, cell cultures, and any groups of plant cells organized into structural and/or functional units. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, Arabidopsis, and woody plants such as coniferous and deciduous trees.

Once a desired gene has been transformed into a particular plant species, it may be propagated in that species or moved into other varieties of the same species, particularly including commercial varieties, using traditional breeding techniques. Alternatively, the coding sequence for a desired protein, e.g., a cellulose-degrading enzyme, may be isolated, genetically engineered for optimal expression and then transformed into the desired variety Preferred cellulase genes to be transformed into plants according to the present invention include, but are not limited to, the *T. fusca* E1 gene (GenBank accession number L20094) (Jung et al. (1993) Appl. Environ. Microbiol. 59:3032-3043); the *T. fusca* E2 gene (GenBank accession number M73321) (Ghangas et al. (1988) Appl. Environ. Microbiol. 54, 2521-2526; Lao et al. (199 1) J. Bacteriol. 173, 3397-3407); and the *T. fusca* E5 gene (GenBank accession number L01577) (Collmer and Wilson (1983) Biotechnology 1, 594-601; Lao et al. (1991) J. Bacteriol. 173, 3397-3407). However, other cellulase genes may be transformed into plants according to the present invention as well, including all of the cellulase genes disclosed in the following references: Collmer et al. (1983) Bio/Technology 1:594-601; Ghangas et al. (1988) Appl. Environ. Microbiol. 54:2521-2526: Wilson (1992) Crit. Rev. Biotechnol. 12:45-63; Jung et al. (1993) Appl. Environ. Microbiol. 59:3032-3043; Lao et al. (1991) J. Bacteriol. 173:3397-3407; and Thomas et al., "Initial Approaches to Artificial Cellulase Systems for Conversion of Biomass to Ethanol"; *Enzymatic Degradation of Insoluble Carbohydrates*, J. N. Saddler and M. H. Penner, eds., ACS Symposium Series 618:208-36, 1995, American Chemical Society, Washington, D.C. These include, but are not limited to, endoglucanases, exoglucanases, and β-D-glucosidases derived from microorganisms such as bacteria and fungi.

Modification of Microbial Genes to Optimize Nuclear Expression in Plants

If desired, the cloned cellulase genes described in this application can be modified for expression in transgenic plant hosts. For example, the transgenic expression in plants of genes derived from microbial sources may require the modification of those genes to achieve and optimize their expression in plants. In particular, bacterial ORFs that encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence will not be required, in which case it is sufficient to isolate a fragment containing the ORF of interest and to insert it downstream of a plant promoter. Preferably, however, as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as *Bacillus*. The modification of such genes can be undertaken using techniques now well known in the art. The following problems are typical of those that may be encountered:

1. Codon Usage

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210) have suggested the sequence GTCGACCATGGTC (SEQ ID NO:1) as a consensus translation initiator for the expression of the E. coli uidA gene in plants. Further, Joshi (NAR 15: 6643-6653 (1987)) has compared many plant sequences adjacent to the ATG and suggests the consensus TAAA-CAATGGCT (SEQ ID NO:2). In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plar species. A survey of 14 maize genes located in the GenBank databas provided the following results:

| Position Before the Initiating ATG in 14 Maize Genes: | | | | | | | | | | |
|---|---|---|---|---|---|---|---|---|---|---|
| | −10 | −9 | −8 | −7 | −6 | −5 | −4 | −3 | −2 | −1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the cellulase genes are being incorporated, and the sequence adjacent to the ATG modified to incorporate the preferred nucleotides.

4. Removal of Illegitimate Splice Sites

Genes cloned from non-plant sources and not optimized for expression in plants may also contain motifs which may be recognized in plants as 5' or 3' splice sites, and be cleaved, thus generating truncated or deleted messages. These sites can be removed using the techniques described in application Ser. No. 07/961,944, hereby incorporated by reference.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy). In most cases it is preferable to assay the expression of gene constructions using transient assay protocols (which are well known in the art) prior to their transfer to transgenic plants.

A major advantage of plastid transformation is that plastids are generally capable of expressing bacterial genes without substantial modification. Coden adaptation, etc. as described above is not required, and plastids are capable of expressing multiple open reading frames under control of a single promoter.

Construction of Plant Transformation Vectors

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, Gene 19: 259-268 (1982); Bevan et al., Nature 304:184-187 (1983)), the bar gene which confers resistance to the herbicide phoSphInothricin (White et al., Nucl Acids Res 18: 1062 (1990), Spencer et al. Theor Appl Genet 79: 625-631(1990)), the hpt gene which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)).

1. Construction of Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below the construction of two typical vectors is described.

Construction of pCIB200 and pCIB2001: The binary vectors pCIB200 and pCIB2001 are used for the construction of recombinant vectors for use with *Agrobacterium* and was constructed in the following manner. pTJS75kan was created by NarI digestion of pTJS75 (Schmidhauser & Helinski, J Bacteriol. 164: 446-455 (1985)) allowing excision of the tetracycline-resistance gene, followed by insertion of an AccI fragment from pUC4K carrying an NPTII (Messing & Vierra, Gene 19: 259-268 (1982); Bevan et al., Nature 304: 184-187 (1983); McBride et al., Plant Molecular Biology 14: 266-276 (1990)). XhoI linkers were ligated to the EcoRV fragment of pCIB7 which contains the left and right T-DNA borders, a plant selectable nos/nptII chimeric gene and the pUC polylinker (Rothstein et al., Gene 53: 153-161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclII AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives thereof: The binary vector pCIB10 contains a gene encoding kanamycin resistance for selection in plants, T-DNA right and left border sequences and incorporates sequences from the wide host-range plasmid pRK252 allowing it to replicate in both *E. coli* and *Agrobacterium*. Its construction is described by Rothstein et al. (Gene 53: 153-161 (1987)). Various derivatives of pCIB10 have been constructed which incorporate the gene for hygromycin B phosphotransferase described by Gritz et al. (Gene 25: 179-188 (1983)). These derivatives enable selection of transgenic plant cells on hygromycin only (pCIB743), or hygromycin and kanamycin (pCIB715, pCIB717).

2. Construction of Vectors Suitable for Non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on *Agrobacterium* include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064: pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93107278. The 35S promoter of this vector contains two ATG sequences 5' of the start site. These sites were mutated using standard PCR techniques in such a way as to remove the ATGs and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the a 400 bp SmaI fragment containing the bar gene from *Streptomyces viridochromogenes* was excised and inserted into the HpaI site of pCIB3060 (Thompson et al. EMBO J 6: 2519-2523 (1987)). This generated pCIB3064 which comprises the bar gene under the control of the CaMV 35S promoter and terminator for herbicide selection, a gene fro ampicillin resistance (for selection in *E. coli*) and a polylinker with the unique sites SphI, PstI, HindIII, and BamHI. This vector is suitable for the cloning of plant expression cassettes containing their own regulatory signals.

Construction of pSOG19 and pSOG35: pSOG35 is a transformation vector which utilizes the *E. coli* gene dihydrofolate reductase (DHFR) as a selectable marker conferring resistance to methotrexate. PCR was used to amplify the 35S promoter (~800 bp), intron 6 from the maize AdhI gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Requirements for Construction of Plant Expression Cassettes

Gene sequences intended for expression in transgenic plants are firstly assembled in expression cassettes behind a suitable promoter and upstream of a suitable transcription terminator. These expression cassettes can then be easily transferred to the plant transformation vectors described above.

1. Promoter Selection

The selection of promoter used in expression cassettes will determine the spatial and temporal expression pattern of the transgene in the transgenic plant. Selected promoters will express transgenes in specific cell types (such as leaf epidermal cells, meosphyll cells, root cortex cells) or in specific tissues or organs (roots, leaves or flowers, for example) and this selection will reflect the desired location of biosynthesis of the cellulase. Alternatively, the selected promoter may drive expression of the gene under a light-induced or other temporally regulated promoter. A further (and preferred) alternative is that the selected promoter be inducible by an external stimulus, e.g., application of a specific chemical inducer or wounding. This would provide the possibility of inducing cellulase transcription only when desired.

2. Transcriptional Terminators

A variety of transcriptional terminators are available for use in expression cassettes. These are responsible for the termination of transcription beyond the transgene and its correct polyadenylation. Appropriate transcriptional terminators and those which are known to function in plants and include the CaMV 35S terminator, the tml terminator, the nopaline synthase terminator, the pea rbcS E9 terminator. These can be used in both monocoylyedons and dicotyledons.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develep 1: 1183-1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15; 65-79 (1990)).

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the aminoterminal end of various proteins and which is cleaved during chloroplast import yielding the mature protein (e.g. Comai et al. J. Biol. Chem. 263: 15104-15109 (1988)). These signal sequences can be fused to heterologous gene products to effect the import of heterologous products into the chloroplast (van den Broeck et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13: 411-418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al. (Proc. Natl. Acad. Sci. USA 82: 6512-6516 (1985)).

In addition, sequences have been characterized which cause the targeting of gene products to other cell compartments. Aminoterminal sequences are responsible for targeting to the ER, the apoplast, and extracellular secretion from aleurone cells (Koehler & Ho, Plant Cell 2: 769-783 (1990)). Additionally, aminoterminal sequences in conjunction with carboxyterminal sequences are responsible for vacuolar targeting of gene products (Shinshi et al. Plant Molec. Biol. 14: 357-368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the aminoterminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081-1091 (1982); Wasmann et al. Mol. Gen. Genet. 205: 446-453 (1986)). These construction techniques are well knownn the art and are equally applicable to mitochondria and peroxisomes. The choice of targeting which may be required for cellulase genes will depend on the cellular localization of the precursor required as the starting point for a given pathway. This will usually be cytosolic or chloroplastic, although it may is some cases be mitochondrial or peroxisomal.

The above-described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

Examples of Expression Cassette Construction

The present invention encompasses the expression of cellulase genes under the regulation of any promoter that is expressible in plants, regardless of the origin of the promoter.

Furthermore, the invention encompasses the use of any plant-expressible promoter in conjunction with any further sequences required or selected for the expression of the cellulase gene. Such sequences include, but are not restricted to, transcriptional terminators, extraneous sequences to enhance expression (such as introns [e.g. Adh intron 1], viral sequences [e. g. TMV-Ω]), and sequences intended for the targeting of the gene product to specific organelles and cell compartments.

1. Constitutive Expression: the CaMV 35S Promoter

Construction of the plasmid pCGN1761 is described in the published patent application EP 0 392 225 (example 23). pCGN1761 contains the "double" 35S promoter and the tml transcriptional terminator with a unique EcoRI site between the promoter and the terminator and has a pUC-type backbone. A derivative of pCGN1761 was constructed which has a modified polylinker which includes NotI and XhoI sites in addition to the existing EcoRI site. This derivative was designated pCGN1761ENX. pCGN1761ENX is useful for the cloning of cDNA sequences or gene sequences (including microbial ORF sequences) within its polylinker for the purposes of their expression under the control of the 35S promoter in transgenic plants. The entire 35S promoter-gene sequence-tml terminator cassette of such a construction can be excised by HindIII, SphI, SalI, and XbaI sites 5' to the promoter and XbaI, BamHI and BglI sites 3' to the terminator for transfer to transformation vectors such as those described above. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter.

2. Modification of pCGN1761ENX by Optimization of the Translational Initiation Site For any of the constructions described in this section, modifications around the cloning sites can be made by the introduction of sequences which may enhance translation.

This is particularly useful when genes derived from microorganisms are to be introduced into plant expression cassettes as these genes may not contain sequences adjacent to their initiating methionine which may be suitable for the initiation of translation in plants. In cases where genes derived from microorganisms are to be cloned into plant expression cassettes at their ATG it may be useful to modify the site of their insertion to optimize their expression. Modification of pCGN1761ENX is described by way of example to incorporate one of several optimized sequences for plant expression (e.g. Joshi, supra).

pCGN1761ENX is cleaved with SphI, treated with T4 DNA polymerase and religated, thus destroying the SphI site located 5' to the double 35S promoter. This generates vector pCGN1761ENX/Sph-. pCGN1761ENX/Sph- is cleaved with EcoRI, and ligated to an annealed molecular adaptor of the sequence 5'-AATTCTAAAGCATGCCGATCGG-3' (SEQ ID NO:3)/5'-AATTCCGATCGGCATGCTTTA-3' (SEQ ID NO:4). This generates the vector pCGNSENX which incorporates the quasi-optimized plant translational initiation sequence TAAA-C adjacent to the ATG which is itself part of an SphI site which is suitable for cloning heterologous genes at their initiating methionine. Downstream of the SphI site, the EcoRI NotI and XhoI sites are retained.

An alternative vector is constructed which utilizes an NcoI site at the initiating ATG. This vector, designated pCGN1761NENX is made by inserting an annealed molecular adaptor of the sequence 5'-AATTCTAAACCATGGC-GATCGG-3' (SEQ ID NO:5)/5'AATTCCGATCGCCATG-GTTTA-3' (SEQ ID NO:6) at the pCGN 1761ENX EcoRI site. Thus, the vector includes the quasi-optimized sequence TAAACC adjacent to the initiating ATG which is within the NcoI site. Downstream sites are EcoRI NotI. and XhoI. Prior to this manipulation, however, the two NcoI sites in the pCGN1761ENX vector (at upstream positions of the 5'35S promoter unit) are destroyed using similar techniques to those described above for SphI or alternatively using "inside-outside" PCR (Innes et al. PCR Protocols: A guide to methods and applications. Academic Press, New York (1990). This manipulation can be assayed for any possible detrimental effect on expression by insertion of any plant cDNA or reporter gene sequence into the cloning site followed by routine expression analysis in plants.

3. Expression Under a Chemically Regulatable Promoter

This section describes the replacement of the double 35S promoter in pCGN1761ENX with any promoter of choice; by way of example, the chemically regulatable PR-1a promoter is described in U.S. Pat. No. 5,614,395, which is hereby incorporated by reference in its entirety, and the chemically regulatable *Arabidopsis* PR-1 promoter is described in U.S. Provisional Application No. 60/027,228, incorporated herein by reference. The promoter of choice is preferably excised from its source by restriction enzymes, but can alternatively be PCR-amplified using primers which carry appropriate terminal restriction sites. Should PCR-amplification be undertaken, then the promoter should be resequenced to check for amplification errors after the cloning of the amplified promoter in the target vector. The chemically regulatable tobacco PR-1a promoter is cleaved from plasmid pCIB1004 (see EP 0 332 104, example 21 for construction) and transferred to plasmid pCGN1761ENX. pCIB1004 is cleaved with NcoI and the resultant 3' overhang of the linearized fragment is rendered blunt by treatment with T4 DNA polymerase. The fragment is then cleaved with HindIII and the resultant PR-1a promoter containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. Selected cellulase genes can be inserted into this vector, and the fusion products (i.e. promoter-gene-terminator) can subsequently be transferred to any selected transformation vector, including those described in this application.

Various chemical regulators may be employed to induce expression of the cellulase coding sequence in the plants transformed according to the present invention. In the context of the instant disclosure, "chemical regulators" include chemicals known to be inducers for the PR-1a promoter in plants, or close derivatives thereof. A preferred group of regulators for the chemically inducible cellulase genes of this invention is based on the benzo-1,2,3-thiadiazole (BTH) structure and includes, but is not limited to, the following types of compounds: benzo-1,2,3-thiadiazolecarboxylic acid, benzo-1,2,3-thiadiazolethiocarboxylic acid, cyanobenzo-1,2,3-thiadiazole, benzo-1,2,3-thiadiazolecarboxylic acid amide, benzo-1,2,3-thiadiazolecarboxylic acid hydrazide, benzo-1,2,3-thiadiazole-7-carboxylic acid, benzo-1,2,3-thiadiazole-7-thiocarboxylic acid, 7-cyanobenzo-1,2,3-thiadiazole, benzo-1,2,3-thiadiazole-7-carboxylic acid amide, benzo-1,2,3-thiadiazole-7-carboxylic acid hydrazide, alkyl benzo-1,2,3-thiadiazolecarboxylate in which the alkyl group contains one to six carbon atoms, methyl benzo-1,2,3-thiadiazole-7-carboxylate, n-propyl benzo-1,2,3-thiadiazole-7-carboxylate, benzyl benzo-1,2,3-thiadiazole-7-carboxylate, benzo-1,2,3-thiadiazole-7-carboxylic acid sec-butylhydrazide, and suitable derivatives thereof. Other chemical inducers may include, for example, benzoic acid, salicylic acid (SA), polyacrylic acid and substituted derivatives thereof; suitable substituents include lower alkyl, lower alkoxy, lower alkylthio, and halogen. Still another group of regulators for the chemically inducible DNA sequences of this invention is based on the pyridine carboxylic acid structure, such as the isonicotinic acid structure and preferably the haloisonicotinic acid structure. Preferred are dichloroisonicotinic acids and derivatives thereof, for example the lower alkyl esters. Suitable regulators of this class of compounds are, for example, 2,6-dichloroisonicotinic acid (INA), and the lower alkyl esters thereof, especially the methyl ester.

4. Constitutive Expression: the Actin Promoter

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163-171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150-160 (1991)). These incorporate the ActI-intron 1, AdhI 5' flanking sequence and AdHI-intron 1 (from the maize alcohol dehydrogenase gene) and sequence from the CaMV 35S promoter. Vectors showing highest expression were fusions of 35S and the ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150-160 (1991)) can be easily modified for the expression of cellulase genes and are particularly suitable for use in monocotyledonous hosts. For example, promoter containing fragments can be removed from the McElroy constructions and used to replace the double 35S promoter in pCGN1761ENX, which is then available for the insertion or specific gene sequences. The fusion genes thus constructed can then be transferred to appropriate transformation vectors. In a separate report the rice ActI promoter with its first intron has also been found to direct high expression in cultured barley cells (Chibbar et al. Plant Cell Rep. 12: 506-509 (1993)).

5. Constitutive Expression: the Ubiquitin Promoter

Ubiquitin is another gene product known to accumulate in many call types and its promoter has been cloned from several species for use in transgenic plants (e.g. sunflower—Binet et al. Plant Science 79: 87-94 (1991), maize—Christensen et al. Plant Molec. Biol. 12: 619-632 (1989)). The maize ubiquitin promoter has been developed in transgenic monocot systems and its sequence and vectors constructed for monocot transformation are disclosed in the patent publication EP 0 342 926 (to Lubrizol). Further, Taylor et al. (Plant Cell Rep. 12: 491495 (1993)) describe a vector (pAHC25) which comprises the maize ubiquitin promoter and first intron and its high activity in cell suspensions of numerous monocotyledons when introduced via microprojectile bombardment. The ubiquitin promoter is suitable for the expression of cellulase genes in transgenic plants, especially monocotyledons. Suitable vectors are derivatives of pAHC25 or any of the transformation vectors described in this application, modified by the introduction of the appropriate ubiquitin promoter and/or intron sequences.

6. Root Specific Expression

Another pattern of expression for the cellulases of the instant invention is root expression. A suitable root promoter is that described by de Framond (FEBS 290: 103-106 (1991)) and also in the published patent application EP 0 452 269 (to Ciba-Geigy). This promoter is transferred to a suitable vector such as pCGN1761ENX for the insertion of a cellulase gene and subsequent transfer of the entire promoter-gene-terminator cassette to a transformation vector of interest.

7. Wound Inducible Promoters

Wound-inducible promoters may also be suitable for the expression of cellulase genes. Numerous such promoters have been described (e.g. Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), Warner et al. Plant J. 3: 191-201 (1993)) and all are suitable for use with the instant invention. Logemann et al. describe the 5' upstream sequences of the dicotyledonous potato wunl gene. Xu et al. show that a wound inducible promoter from the dicotyledon potato (pin2) is active in the monocotyledon rice. Further, Rohrmeier & Lehle describe the cloning of the maize Wipl cDNA which is wound induced and which can be used to isolated the cognate promoter using standard techniques. Similarly, Firek et al. and Warner et al. have described a wound induced gene from the monocotyledon Asparagus officinalis which is expressed at local wound and pathogen invasion sites. Using cloning techniques well known in the art, these promoters can be transferred to suitable vectors, fused to the cellulase genes of this invention, and used to express these genes at the sites of plant wounding.

8. Pith-Preferred Expression

Patent Application WO 93/07278 (to Ciba-Geigy) describes the isolation of the maize trpA gene which is preferentially expressed in pith cells. The gene sequence and promoter extend up to −1726 from the start of transcription are presented. Using standard molecular biological techniques, this promoter or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

9. Leaf-Specific Expression

A maize gene encoding phosphoenol carboxylase (PEPC) has been described by Hudspeth & Grula (Plant Molec Biol 12: 579-589 (1989)). Using standard molecular biological techniques the promoter for this gene can be used to drive the expression of any gene in a leaf-specific manner in transgenic plants.

10. Expression with Chloroplast Targeting

Chen & Jagendorf (J. Biol. Chem. 268: 2363-2367 (1993) have described the successful use of a chloroplast transit peptide for import of a heterologous transgene. This peptide used is the transit peptide from the rbcS gene from *Nicotiana plumbaginifolia* (Poulsen et al. Mol. Gen. Genet. 205: 193-200 (1986)). Using the restriction enzymes DraI and SphI, or Tsp509I and SphI the DNA sequence encoding this transit peptide can be excised from plasmid prbcS-8B and manipulated for use with any of the constructions described above. The DraI-SphI fragment extends from −58 relative to the initiating rbcS ATG to, and including, the first amino acid (also a methionine) of the mature peptide immediately after the import cleavage site, whereas the Tsp509I-SphI fragment extends from −8 relative to the initiating rbcS ATG to, and including, the first amino acid of the mature peptide. Thus, these fragments can be appropriately inserted into the polylinker of any chosen expression cassette generating a transcriptional fusion to the untranslated leader of the chosen promoter (e.g. 35S, PR-1a, actin, ubiquitin etc.), whilst enabling the insertion of a cellulase gene in correct fusion downstream of the transit peptide. Constructions of this kind are routine in the art. For example, whereas the DraI end is already blunt, the 5' Tsp509I site may be rendered blunt by T4 polymerase treatment, or may alternatively be ligated to a linker or adaptor sequence to facilitate its fusion to the chosen promoter. The 3' SphI site may be maintained as such, or may alternatively be ligated to adaptor of linker sequences to facilitate its insertion into the chosen vector in such a way as to make available appropriate restriction sites for the subsequent insertion of a selected cellulase gene. Ideally the ATG of the SphI site is maintained and comprises the first ATG of the selected cellulase gene. Chen & Jagendorf provide consensus sequences for ideal cleavage for chloroplast import, and in each case a methionine is preferred at the first position of the mature protein. At subsequent positions there is more variation and the amino acid may not be so critical. In any case, fusion constructions can be assessed for efficiency of import in vitro using the methods described by Bartlett et al. (In: Edelmann et al. (Eds.) Methods in Chloroplast Molecular Biology, Elsevier. pp 1081-1091 (1982)) and Wasmann et al. (Mol. Gen. Genet.

205: 446453 (1986)). Typically the best approach may be to generate fusions using the selected cellulase gene with no modifications at the aminoterminus, and only to incorporate modifications when it is apparent that such fusions are not chloroplast imported at high efficiency, in which case modifications may be made in accordance with the established literature (Chen & Jagendorf; Wasman et al.; Ko & Ko, J. Biol. Chem. 267: 13910-13916 (1992)).

A preferred vector is constructed by transferring the DraI-SphI transit peptide encoding fragment from prbcS-8B to the cloning vector pCGN1761ENX/SPh. This plasmid is cleaved with EcoRI and the termini rendered blunt by treatment with T4 DNA polymerase. Plasmid prbcS-8B is cleaved with SphI and ligated to an annealed molecular adaptor of the sequence 5'-CCAGCTGGAATTCCG-3' (SEQ ID NO:7)/5'-CGGAATTCCAGCTGGCATG-3' (SEQ ID NO:8). The resultant product is 5'-terminally phosphorylated by treatment with T4 kinase. Subsequent cleavage with DraI releases the transit peptide encoding fragment which is ligated into the blunt-end ex-EcoRI sites of the modified vector described above. Clones oriented with the 5' end of the insert adjacent to the 3' end of the 35S promoter are identified by sequencing. These clones carry a DNA fusion of the 35S leader sequence to the rbcS-8A promoter-transit peptide sequence extending from −58 relative to the rbcS ATG to the ATG of the mature protein, and including at that position a unique SphI site, and a newly created EcoRI site, as well as the existing NotI and XhoI sites of pCGN1761ENX. This new vector is designate pCGN 1761/CT. DNA sequences are transferred to pCGN1761/CT it frame by amplification using PCR techniques and incorporation of at SphI, NSphI, or NlaIII site at the amplified ATG, which following restriction enzyme cleavage with the appropriate enzyme is ligated into SphI-cleaved pCGN1761/CT. To facilitate construction, it may be required to change the second amino acid of cloned gene, however, in almost all cases the use of PCR together with standard site directed mutagenesis will enable the construction of any desired sequence around the cleavage site and first methionine of the mature protein.

A further preferred vector is constructed by replacing the double 35S promoter of pCGN1761ENX with the BamHI-SphI fragment of prbcS-8A which contains the full-length light regulated rbcS-8A promoter from −1038 (relative to the transcriptional start site) up to the first methionine of the mature protein. The modified pCGN1761 with the destroyed SphI site is cleaved with PstI and EcoRI and treated with T4 DNA polymerase to render termini blunt. prbcS-8A is cleaved SphI and ligated to the annealed molecular adaptor of the sequence described above. The resultant product is 5'-terminally phosphorylated by treatment with T4 kinase. Subsequent cleavage with BamHI releases the promoter-transit peptide containing fragment which is treated with T4 DNA polymerase to render the BamHI terminus blunt. The promoter-transit peptide fragment thus generated is cloned into the prepared pCGN1761ENX vector, generating a construction comprising the rbcS-8A promoter and transit peptide with an SphI site located at the cleavage site for insertion of heterologous genes. Further, downstream of the SphI site there are EcoRI (re-created), NotI, and XhoI cloning sites. This construction is designated pCGN1761 rbcS/CT.

Similar manipulations can be undertaken to utilize other GS2 chloroplast transit peptide encoding sequences from other sources (monocotyledonous and dicotyledonous) and from other genes. In addition, similar procedures can be followed to achieve targeting to other subcellular compartments such as mitochondria.

Transformation of Dicotyledons

Transformation techniques for dicotyledons are well known in the art and include *Agrobacterium*-based techniques and techniques which do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. The many crop species which are routinely transformable by *Agrobacterium* include tobacco, tomato, sunflower, cotton, oilseed rape, potato, soybean, alfalfa and poplar (EP 0 317 511 (cotton [1313]), EP 0 249 432 (tomato, to Calgene), WO 87107299 (Brassica, to Calgene), U.S. Pat. No. 4,795,855 (poplar)). *Agrobacterium* transformation typically involves the transfer of the binary vector carrying the foreign DNA of interest (e.g. pCIB2000 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höbfgen & Willmitzer, Nucl. Acids Res. 16: 9877(1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435 ([1280/1281] to Ciba-Geigy), EP 0 392 225 (to Ciba-Geigy) and WO 93/07278 (to Ciba-Geigy) describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, application WO 93/07278 (to Ciba-Geigy) and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for *Japonica*-types and *Indica*-types (Zhang et al., Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al. (Biotechnology 10: 667-674 (1992)) using particle bombardment into cells of type C long-term regenerable callus, and also by Vasil et al. (Biotechnology 11: 1553-1558 (1993)) and Weeks et al. (Plant Physiol. 102: 1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. Patent application No. 08/147,161 describes methods for wheat transformation and is hereby incorporated by reference.

Chloroplast Transformation

Plastid transformation technology is extensively described in U.S. Pat. Nos. 5,451,513, 5,545,817, and 5,545,818, all of which are hereby expressly incorporated by reference in their entireties; in PCT application no. WO 95/16783, which is hereby incorporated by reference in its entirety; and in McBride et al. (1994) Proc. Natl. Acad. Sci. USA 91, 7301-7305, which is also hereby incorporated by reference in its entirety. The basic technique for chloroplast transformation involves introducing regions of cloned plastid DNA flanking a selectable marker together with the gene of interest into a sutable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin andlor streptomycin were utilized as selectable markers for transformation (Svab, Z., Hajdukiewicz, P., and Maliga, P. (1990) Proc. Natl. Acad. Sci. USA 87, 8526-8530, hereby incorporated by reference; Staub, J. M., and Maliga, P. (1992) Plant Cell 4, 39-45, hereby incorporated by reference). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) *EMBO J.* 12, 601-606, hereby incorporated by reference). Substantial increases in transformation frequency were obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci. USA* 90, 913-917, hereby incorporated by reference). Previously, this marker had been used successfully for high-frequency transformation of the plastid genome of the green alga *Chlamydomonas reinhardtii* (Goldschmidt-Clermont, M. (1991) *Nucl. Acids Res.* 19, 4083-4089, hereby incorporated by reference). Other selectable markers useful for plastid transformation are known in the art and encompassesd within the scope of the invention. Typically, approximately 15-20 cell division cycles following transformation are required to reach a homoplastidic state.

Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. However, such high expression levels may pose potential viability problems, especially during early plant growth and development. Similar problems are posed by the expression of bioactive enzymes or proteins that may be highly deleterious to the survival of transgenic plants and henced if expressed constitutively may not be introduced successfully into the plant genome. Thus, in one aspect, the present invention has coupled expression in the nuclear genome of a choroplast-targeted phage T7 RNA polymerase under control of the chemically inducible PR-1a promoter (U.S. Pat. No. 5,614,395 incorporated by reference) of tobacco to a chloroplast reporter transgene regulated by T7 gene 10 promoter/terminator sequences. For example, when plastid transformants homoplasmic for the maternally inherited uidA gene encoding the β-glucuronidase (GUS) reporter are pollinated by lines expressing the T7 polymerase in the nucleus, F1 plants are obtained that carry both transgene constructs but do not express the GUS protein. Synthesis of large amounts of enzymatically active GUS is triggered in plastids of these plants only after foliar application of the PR-1a inducer compound benzo(1,2,3)thiadiazole-7-carbothioic acid S-methyl ester (BTH). As set forth below in Section C of the Examples, the present invention also entails the synthesis of large amounts of cellulose-degrading enzymes using this chloroplast-targeted T7 RNA polymerase expression system.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by J. Sambrook, E. F. Fritsch and T. Maniatis, *Molecular Cloning: A Laboratory manual*, Cold Spring Harbor laboratory, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

A. Expression of Cellulases in the Plant Cytosol

Example A1

Preparation of a Chimeric Gene Containing the *T. fusca* E1 Cellulase Coding Sequence Fused to the Tobacco PR-1a Promoter Plasmid pGFE1 (Jung et al. (1993) Appl. Environ. Microbiol. 59, 3032-3043) containing the *T. fusca* E1 gene (GenBank accession number L20094), which codes for a protein with endoglucanase activity, was used as the template for PCR with a left-to-right "top strand" primer comprising an ATG before the first codon of the mature E1 protein, the first 21 base pairs of the mature protein and a NcoI restriction site at the newly created ATG (primer E11: GCG CCC ATG GAC GAA GTC AAC CAG ATT CGC) (SEQ ID NO:9) and a right-to-left "bottom strand" primer homologous to positions 322 to 346 from the newly created ATG of the E1 gene (primer E12: CCA GTC GAC GTT GGA GGT GAA GAC) (SEQ ID NO:10). This PCR reaction was undertaken with AmpliTaq DNA polymerase according to the manufacturer's recommendations (Perkin Elmer/Roche, Branchburg, N.J.) for five cycles at 94° C. (30 s), 40° C. (60 s), and 72° C. (30 s) followed by 25 cycles at 94° C. (30 s), 55° C. (60 s) and 72° C. (30 s). This generated a product of 352 bp containing a NcoI site at its left end and a EcoRI site at its right end and comprised the 5' end of the E1 gene without the signal sequence. The fragment was gel purified using standard procedures, cleaved with NcoI and EcoRI (all restriction enzymes purchased from Promega, Madison, Wis. or New England Biolabs, Beverly, Mass.) and ligated into the NcoI and EcoRI sites of pTC191 (De La Fuente el al. (1994) Gene 139, 83-86) to obtain pE1.

Plasmid pGFE1 was then digested with EcoRI and ScaI. The 3.0 kb long EcoRI fragment containing the 3' end of the E1 gene was gel purified and ligated with pE1, which had previously been digested with EcoRI, to obtain pCTEI containing the entire E1 gene without a signal sequence. Plasmid pCTE1 was digested with NcoI and SacI. The 3.3 kb long fragment containing the E1 gene was gel purified and ligated into the NcoI and SacI sites of pJG203 between a 903 bp long tobacco PR-1a promoter and the nos gene termination signals (Uknes et al. (1993), The Plant Cell 5,159-169, modified by removal of an additional SacI site, Joern Goerlach, notebook no. 2941, pp 4-9 and 13-15), yielding pTPRIE1 containing the E1 gene fused to the tobacco PR-1a promoter (FIG. 1).

Plasmid pTPRIE1 was digested with XhoI and XbaI and the 4.5 kb long fragment containing the chimeric E1 gene construct was gel purified and ligated into the XhoI and XbaI sites of pBHYGM to obtain binary vector pEGL101. pBHYGM is a modified pGPTV-Hyg vector (Becker et al. (1992) Plant Mol. Biol. 20, 1195-1197) produced by insertion of a polylinker containing BfrI/ApaI/ClaI/SmaI/BfrI/XbaI/SalI/PstI/SphI/HindIII restriction sites into the EcoRI and XbaI sites of pGPTV-Hyg.

Example A2

Preparation of a Chimeric Gene Containing the *T. fusca* E2 cellulase Coding Sequence Fused to the Tobacco PR-1a Promoter Plasmid pJT17 containing the *T. fusca* E2 gene (Ghangas et al. (1988) Appl. Environ. Microbiol. 54, 2521-2526; Lao et al. (1991) J. Bacteriol. 173, 3397-3407) (GenBank accession number M73321), which codes for a protein with cellobiohydrolase activity, was used as the template for PCR with a left-to-right "top strand" primer comprising an ATG before the last codon of the E2 signal sequence, the first 18 base pairs of the mature protein and a NcoI restriction site at the newly created ATG (primer E21: GCG CGC CAT GGC CAA TGA TTC TCC GTT CTA C) (SEQ ID NO:11) right-to-left "bottom strand" primer homologous to positions 310 to 334 from the newly created ATG of the E2 gene (primer E22: GGG ACG GTT CTT CAG TCC GGC AGC) (SEQ ID NO:12). This PCR reaction was undertaken with AmpliTaq DNA polymerase according to the manufacturer's recommendations for five cycles at 94° C. (30 s), 40° C. (60 s), and 72° C. (30 s) followed by 25 cycles at 94° C. (30 s), 55° C. (60 s) and 72° C. (30 s). This generated a product of 341 bp containing a NcoI site at its left end and a EcoRI site at its right end comprising the 5' end of the E2 gene without a signal sequence. The fragment was gel purified using standard procedures, cleaved with NcoI and EcoRI and ligated into the NcoI and EcoRI sites of pTC191 to obtain pE2.

Plasmid pJT17 was then digested with EcoRI and SacI. The 1.7 kb long fragment containing the 3' end of the E2 gene was gel purified and ligated with pE2, which had previously been digested with EcoRI and SacI, to obtain pCTE2 containing the entire E2 gene without a signal sequence. Plasmid pCTE2 was digested with NcoI and SacI and the 2.0 kb long fragment containing the E2 gene was gel purified and ligated into the NcoI and SacI sites of pJG203, yielding pTPR1E2 containing the E2 gene fused to a 903 bp long tobacco PR-1a promoter fragment (FIG. 1).

Plasmid pTPR1E2 was digested with XhoI and XbaI and the 2.9 kb long fragment containing the chimeric E2 gene construct was gel purified and ligated into the XhoI and XbaI sites of pBHYGM to construct pEGL102.

Example A3

Preparation of a Chimeric Gene Containing the *T. fusca* E5 Cellulase Coding Sequence Fused to the Tobacco PR-1a Promoter Plasmid pD374, a modified version of pD370 (Collmer and Wilson (1983) Biotechnology 1, 594-601; Lao et al. (1991) J. Bacteriol. 173, 3397-3407) containing the *T. fusca* E5 gene (GenBank accession number L01577), which codes for a protein with endoglucanase activity, was used as the template for PCR with a left-to-right "top strand" primer comprising an ATG before the first codon of the mature E5 protein, the first 21 base pairs of the mature protein and a NcoI restriction site at the newly created ATG (primer E51: CGC CCA TGG CCG GTC TCA CCG CCA CAG TC) (SEQ ID NO:13) and a right-to-left "bottom strand" primer homologous to positions 89 to 114 from the newly created ATG of the E5 gene (primer E52: GAC GAC CTC CCA CTG GGA GAC GGT G) (SEQ ID NO:14). AmpliTaq DNA polymerase was used for PCR according to the manufacturer's recommendations for five cycles at 94° C. (30 s), 40° C. (60 s), and 72° C. (30 s) followed by 25 cycles at 94° C. (30 s), 55° C. (60 s) and 72° C. (30 s). This generated a product of 119 bp containing a NcoI site at its left end and a XhoI site at its right end and comprised the 5' end of the E5 gene without a signal sequence. The fragment was gel purified, cleaved with NcoI and XhoI and ligated into the NcoI and XhoI sites of pCIB4247 to obtain pCE5. pCIB4247 is a pUC19 derivative (Yanisch-Perron et al. (1985) Gene 33, 103-119) containing a polylinker with NcoI, XhoI and EcoRI restriction sites.

In order to reconstitute the entire E5 gene, a 1.4 kb long XhoI/PvuII fragment of pD374 containing the E5 gene 3' end was subcloned into the XhoI and EcoRV sites of pICEM19R+, a pUC19 derivative containing a polylinker with XhoI, EcoRV and EcoRI restriction sites, excised as a XhoI/EcoRI fragment and ligated into the XhoI and EcoRI sites of pCE5 to form pCTE5 containing the entire E5 gene. pCTE5 was digested with EcoRI, the protruding ends of the EcoRI site were filled-in with DNA Polymerase I Klenow fragment (Promega, Madison, Wis.) and plasmid DNA was further digested with NcoI. The 1.5 kb long fragment containing the E5 gene was gel purified and ligated into the NcoI and EcoICRI sites of pJG203, yielding pTPR1E5 containing the E5 gene fused to a 903 bp long tobacco PR-1a promoter (FIG. 1).

Plasmid pTPR1E5 was digested with ApaI, XbaI and SacI and the 2.7 kb long ApaI/XbaI fragment containing the chimeric E5 gene construct was gel purified and ligated into the ApaI and XbaI sites of pBHYGM to construct pEGL105.

Example A4

Preparation of a Chimeric Gene Containing the *T. fusca* E5 Cellulase Coding Sequence Fused to the CaMV 35S Promoter A 1.5 kb long NcoI/EcoRI fragment of pCTE5 containing the E5 gene and whose protruding ends had been previously filled-in with Klenow DNA Polymerase was gel purified and ligated into the filled-in EcoRI site of pCGN1761 between a duplicated CaMV 35S promoter (Kay el al. (1987) Science 236, 1299-1302) and the tml gene termination signals (Ream et al. (1983) Proc. Natl. Acad. Sci. USA 80, 1660-1664), resulting in p35SE5 (FIG. 1). A 4.6 kb long fragment of p35SE5 containing the chimeric gene was inserted into the XbaI site of pBHYGM to obtain pEGL355.

Example A5

Preparation of Chimeric Genes Containing the *T. fusca* E1 Cellulase Coding Sequence Fused to the CaMV 35S Promoter A 3.3 kb long NcoI (filled in)/SacI fragment of pCTE1 containing the E1 gene is gel purified and ligated into the filled-in EcoRI site of pCGN1761. The chimeric gene containing the E1 coding sequence fused to the CaMV 35S promoter is inserted into the XbaI site of pBHYGM.

Example A6

Preparation of Chimeric Genes Containing the *T. fusca* E2 Cellulase Coding Sequence Fused to the CaMV 35S Promoter A 2.0 kb long NcoI (filled in)/SacI fragment of pCTE2 containing the E2 gene is gel purified and ligated into the filled-in EcoRI site of pCGN1761. The chimeric gene containing the E2 coding sequence fused to the CaMV 35S promoter is inserted into the XbaI site of pBHYGM.

Example A7

Transformation of Tobacco Leaf Discs by *A. tumefaciens*

The binary vector constructs pEGL101, pEGL102, pEGL105, and pEGL355 were transformed into *A. tumefaciens* strain GV3101 (Bechtold, N. et al. (1993), CR Acad. Sci. Paris, Sciences de la vie, 316:1194-1199) by electroporation (Dower, W. J. (1987), Plant Mol. Biol. Reporter 1:5). The same procedure is used for transformation of tobacco with other constructs containing chimeric cellulase genes.

Leaf discs of *Nicotiana tabacum* cv 'Xanthi nc' and of transgenic line "NahG" overexpressing a salicylate hydroxylase gene (Gaffney et al. (1993) Science 261: 754-756) were cocultivated with *Agrobacterium* clones containing the above mentioned constructs (Horsch et al. (1985), Science 227: 1229-1231) and transformants were selected for resistance to 50 µg/ml hygromycin B. Approximately 50 independent hygromycin lines (T0 lines) for each construct were selected and rooted on hormone-free medium.

Example A8

Transformation of Maize

Maize transformation by particle bombardment of immature embryos is performed as described by Koziel et al. (Biotechnology 11, 194-200, 1993).

Example A9

Transformation of Wheat

Transformation of immature wheat embryos and immature embryo-derived callus using particle bombardment is performed as described by Vasil et. al. (Biotechnology 11: 1553-1558,1993) and Weeks et. al. (Plant Physiology 102: 1077-1084, 1993).

Example A10

Selection of Transgenic Lines with Inducible Cellulase Gene Expression

For each transgenic line, duplicate leaf punches of approximately 2-3 cm$^2$ were incubated for 2 days in 3 ml of benzo(1,2,3)thiadiazole-7-carbothioic acid S-methyl ester (BTH, 5.6 mg/10 ml) or sterile distilled water under ca. 300 μmol/m$^2$/s irradiance. Leaf material was harvested, flash frozen and ground in liquid nitrogen. Total RNA was extracted (Verwoerd et al. (1989) NAR 17, 2362) and Northern blot analysis was carried out as described (Ward et al. (1991) The Plant Cell 3, 1085-1094) using radiolabelled probes specific for each cellulase gene.

Transgenic lines with high levels of inducible transgene expression were allowed to flower and self-pollinate, producing T1 seeds. Ten T1 seeds for each transgenic lines were germinated in soil and the resulting plants self-pollinated. T2 seeds from these plants were germinated on T agar medium (Nitsch and Nitsch (1969) Science 163, 85-87) containing 50 μg/ml hygromycin B to identify lines homozygous for the selectable marker and linked transgene.

Example A11

Induction of Cellulase Expression in Transgenic Plants

Seeds of homozygous nuclear transformant lines are germinated aseptically on T agar medium and incubated at 300 μmol/m$^2$/s irradiance for approximately 4-6 weeks. Alternatively, seeds are germinated in soil and grown in the greenhouse for approximately 2 months. Material of lines expressing cellulase genes under constitutive expression (CAMV 35S promoter) is harvested and flash frozen in liquid nitrogen directly, while lines containing cellulase genes fused to the chemically inducible PR-1a promoter are first sprayed with either 1 mg/ml BTH or water, incubated for 1 to 7 days, and material harvested and flash frozen.

Example A12

Determination of Cellulase Content of Transgenic Plants

In order to determine the amount of cellulase present in the tissues of transgenic plants, chemiluminescent (Amersham) Western blot analysis is performed according to the manufacturer's instructions and Harlow and Lane (1988) Antibodies: A laboratory manual, Cold Spring Harbor Laboratory, Cold Spring Harbor using antisera raised against the E1, E2 and E5 proteins and purified E1, E2 and E5 protein standards (provided by D. Wilson, Cornell University, Ithaca, N.Y.).

Example A13

Determination of Cellulase Activity in Transgenic Plants

Leaf material is harvested as described above and homogenized in PC buffer (50 mM phosphate, 12 mM citrate, pH 6.5). A standard curve (10 nanomolar to 10 micromolar) is prepared by diluting appropriate amounts of 4-methylumbelliferone (MU, Sigma Cat. No. M1381) in PC buffer. Duplicate 100 μl aliquots of each standard and duplicate 50 μl aliquots of each sample are distributed to separate wells of a 96-well microtiter plate. 50 μl of 2 mM 4-methylumbelliferyl-b-D-cellobiopyranoside (MUC, Sigma Cat. No. M6018) prepared in PC buffer is then added to each sample well and the plate is sealed to prevent evaporation and incubated for 30 minutes at 55° C. or at other temperatures ranging from 37° C. to 65° C. The reaction is stopped by adding 100 μl of 0.15 M glycine/NaOH (pH 10.3) and the MU fluorescence emission at 460 nm resulting from cellulase activity is measured with a microplate fluorometer (excitation wavelength=355 nm).

B. Vacuole-Targeted Expression of Cellulases

Example B1

Preparation of a Chimeric Gene Containing the *T. fusca* E5 Cellulase Coding Sequence Fused to the Tobacco PR-1a Promoter Plasmid pD374 containing the *T. fusca* E5 gene (see Example A3) was used as template for PCR with a left-to-right "top strand" primer extending from position 1,135 to 1,156 in the E5 gene relative to the endogenous ATG and comprising an additional NcoI site at its left end (primer VAC1: CAT GCC ATG GGT GAG GCC TCC GAG CTG TTC C) (SEQ ID NO:15) and a right-to-left "bottom strand" primer whose sequence was homologous to the 21 last bp of the E5 gene and including 21 bp of a vacuolar targeting sequence derived from a tobacco chitinase gene (Shinshi et al. (1990) Plant Mol. Biol. 14, 357-368, Neuhaus et al. (1991) Proc. Natl. Acad. Sci. USA 88, 10362-10366), the stop codon of the same tobacco chitinase gene and a SacI restriction site (primer VAC2: TGC GAG CTC TTA CAT AGT ATC GAC TAA AAG TCC GGA CTG GAG CTT GCT CCG CAC) (SEQ ID NO:16). AmpliTaq DNA polymerase was used for PCR according to the manufacturer's recommendations for five cycles at 94° C. (30 s), 40° C. (60 s), and 72° C. (30 s) followed by 25 cycles at 94° C. (30 s), 55° C. (60 s) and 72° C. (30 s). This generated a product of 283-bp containing the 3' end of the E5 gene fused to the vacuolar targeting sequence. The fragment was gel purified, cleaved with NcoI and SacI and ligated into the NcoI and SacI sites of pJG203 to obtain pJGDE5.

Plasmid pD374 was then digested with NcoI and SacI, the 1.1 kb long fragment containing the 5' end of the E5 gene including the signal sequence gel purified and ligated into the NcoI and SacI sites of pJGDE5 to obtain pVACE5 containing the complete E5 gene with signal sequence and vacuolar targeting sequence fused to a 903 bp long tobacco PR-1a promoter (FIG. 1).

Plasmid pVACE5 was digested with ApaI, XbaI and ScaI and the resulting 2.8 kb fragment containing the chimeric E5 gene was gel purified and ligated into the ApaI and XbaI sites of pBHYGM to obtain pEGL115.

Example B2

Preparation of a Chimeric Gene Containing the *T. fusca* E1 Cellulase Coding Sequence Fused to the Tobacco PR-1a Promoter A binary *Agrobacterium* transformation vector containing the *T. fusca* E1 cellulase coding sequence, its signal sequence, and a vacuolar targeting sequence fused to the tobacco PR-1a promoter is constructed as described in Example B1 for the *T. fusca* E5 cellulase coding sequence.

Example B3

Preparation of a Chimeric Gene Containing the *T. fusca* E2 Cellulase Coding Sequence Fused to the Tobacco PR-1 a Promoter A binary *Agrobacterium* transformation vector containing the *T. fusca* E2 cellulase coding sequence, its signal sequence, and a vacuolar targeting sequence fused to the tobacco PR-1 a promoter is constructed as described in Example B1 for the *T. fusca* E5 cellulase coding sequence.

Example B4

Preparation of a Chimeric Gene Containing the *T. fusca* E5 Cellulase Coding Sequence Fused to the CaMV 35S Promoter Plasmid pVACE5 was digested with NcoI and EcoICRI. The resulting 1.6 kb fragment whose protruding NcoI ends had been previously filled-in with Klenow DNA Polymerase was gel purified and ligated into the filled-in EcoRI site of pCGN1761 to obtain p35SVACE5, containing the E5 gene with signal sequence and vacuolar targeting sequence fused to the CaMV 35S promoter (FIG. 1). A 4.7 kb long fragment of p35SE5 containing the chimeric E5 gene was inserted into the XbaI site of pBHYGM to construct pEGL315.

Example B5

Preparation of a Chimeric Gene Containing the *T. fusca* E1 Cellulase Coding Sequence Fused to the CaMV 35S Promoter A binary *Agrobacterium* transformation vector containing the *T. fusca* E1 cellulase coding sequence, its signal sequence, and a vacuolar targeting sequence fused the CaMV 35S promoter is constructed as described in Example B4 for the *T. fusca* E5 cellulase coding sequence.

Example B6

Preparation of a Chimeric Gene Containing the *T. fusca* E2 Cellulase Coding Sequence Fused to the CaMV 35S Promoter A binary *Agrobacterium* transformation vector containing the *T. fusca* E2 cellulase coding sequence, its signal sequence, and a vacuolar targeting sequence fused to the CaMV 35S promoter is constructed as described in Example B4 for the *T. fusca* E5 cellulase coding sequence.

Example B7

Transformation of Tobacco Leaf Discs by *A. tumefaciens*

The binary vector constructs pEGL115 and pEGL315 were transformed into *A. tumefaciens* strain GV3101 (Bechtold, N. et al. (1993), CR Acad. Sci. Paris, Sciences de la vie, 316:1194-1199) by electroporation (Dower, W. J. (1987), Plant Mol. Biol. Reporter 1:5). The same procedure is used for transformation of tobacco with other constructs containing chimeric cellulase genes.

Leaf discs of *Nicotiana tabacum* cv 'Xanthi nc' and of transgenic line "NahG" overexpressing a salicylate hydroxylase gene (Gaffney et al. (1993) Science 261: 754-756) were cocultivated with *Agrobacterium* clones containing the above mentioned constructs (Horsch et al. (1985), Science 227: 1229-1231) and transformants were selected for resistance to 50 µg/ml hygromycin B. Approximately 50 independent hygromycin lines (T0 lines) for each construct were selected and rooted on hormone-free medium.

Example B8

Transformation of Maize

Maize transformation by particle bombardment of immature embryos is performed as described by Koziel et al. (Biotechnology 11, 194-200, 1993).

Example B9

Transformation of Wheat

Transformation of immature wheat embryos and immature embryo-derived callus using particle bombardment is performed as described by Vasil et. al. (Biotechnology 11: 1553-1558,1993) and Weeks et. al. (Plant Physiology 102: 1077-1084, 1993).

Example B10

Selection of Transgenic Lines with Inducible Cellulase Gene Expression

For each transgenic line duplicate leaf punches of approximately 2-3 cm$^2$ were incubated for 2 days in 3 ml of benzo(1,2,3)thiadiazole-7-carbothioic acid S-methyl ester (BTH, 5.6 mg/10 ml) or sterile distilled water under ca. 300 µmol/m$^2$/s irradiance. Leaf material was harvested, flash frozen and ground in liquid nitrogen. Total RNA was extracted (Verwoerd et al. (1989) NAR 17, 2362) and Northern blot analysis was carried out as described (Ward et al. (1991) The Plant Cell 3, 1085-1094) using radiolabelled probes specific for each cellulase gene.

Transgenic lines with high levels of inducible transgene expression were allowed to flower and self-pollinate, producing T1 seeds. Ten T1 seeds for each transgenic lines were germinated in soil and the resulting plants self-pollinated. T2 seeds from these plants were germinated on T agar medium (Nitsch and Nitsch (1969) Science 163, 85-87) containing 50 µg/ml hygromycin B to identify lines homozygous for the selectable marker and linked transgene.

Example B11

Induction of Cellulase Expression in Transgenic Plants

Seeds of homozygous nuclear transformant lines are germinated aseptically on T agar medium and incubated at 300 µmol/m$^2$/s irradiance for approximately 4-6 weeks. Alternatively, seeds are germinated in soil and grown in the greenhouse for approximately 2 months. Material of lines expressing cellulase genes under constitutive expression (CaMV 35S promoter) is harvested and flash frozen in liquid nitrogen directly, while lines containing cellulase genes fused to the chemically inducible PR-1a promoter are first sprayed with either 1 mg/ml BTH or water, incubated for 1 to 7 days, and material harvested and flash frozen.

Example B12

Determination of Cellulase Content of Transgenic Plants

In order to determine the amount of cellulase present in the tissues of transgenic plants, chemiluminescent (Amersham) Western blot analysis is performed according to the manufacturer's instructions and Harlow and Lane (1988) Antibodies: A laboratory manual, Cold Spring Harbor Laboratory, Cold Spring Harbor using antisera raised against the E1, E2 and E5 proteins and purified E1, E2 and E5 protein standards (provided by D. Wilson, Cornell University, Ithaca, N.Y).

Example B13

Determination of Cellulase Activity in Transgenic Plants

1. Fluorometric Assay

Leaf material is harvested as described above and homogenized in PC buffer (50 mM phosphate, 12 mM citrate, pH 6.5). A standard curve (10 nanomolar to 10 micromolar) is prepared by diluting appropriate amounts of 4-methylumbelliferone (MU, Sigma Cat. No. M-1381) in PC buffer. Duplicate 100 µl aliquots of each standard and duplicate 50 µl aliquots of each sample are distributed to separate wells of a 96-well microtiter plate. 50 µl of 2 mM 4-methylumbelliferyl-b-D-cellobiopyranoside (MUC, Sigma Cat. No. M6018), prepared in PC buffer is then added to each well and the plate is sealed to prevent evaporation and then incubated for 30 minutes at the desired temperature (55_C.-60_C. is optimal for $T.$ $fusca$ cellulases). The reaction is stopped by adding 100 µl of 0.15 M glycine/NaOH (pH 10.3) and the fluorescence emission at 460 nm measured with a microplate fluorometer (excitation wavelength=355 nm). In order to calculate the cellulase specific activity (pmoles MU/mg protein/minute) the amount of protein in each extract is determined using a BCA assay (Pierce, Rockford, Ill.) according to the manufacturer's recommendations.

2. CMCase Activity (According to Wilson (1988) Methods in Enzymology, 160: 314-315)

Leaf material is homogenized in 0.3 ml of 0.05 M potassium phosphate buffer (pH 6.5) and is incubated with 0.1 ml of carboxymethylcellulose (CMC, Sigma , Cat. No. C-5678) for 15-60 minutes at the desired temperature (55_C.-60_C. is optimal for $T.$ $fusca$ cellulases). After adding 0.75 ml of DNS reagent (200 g/l sodium potassium tartrate, 10 g/l dinitrosalicylic acid, 2 g/l phenol, 0.5 g/l sodium sulfite, 10 g/l sodium hydroxide) the samples are boiled for 15 minutes. The samples are cooled down and the optical density is measured at 600 nm. The amount of reducing sugars released from CMC is determined using a glucose standard curve and the cellulase activity is expressed in mmol glucose equivalent reducing sugar per minute. In order to calculate the specific cellulase activity the amount of protein in each extract is determined using a BCA assay (Pierce, Rockford, Ill.) according to the manufacturer's recommendations.

Alternatively, the cellulase activity on CMC is measured with a viscosity method as described by Durbin and Lewis (1988) Methods in Enzymology, 160: 314-315.

3. Filter Paper Assay (According to Wilson (1988) Methods in Enzymology, 160: 314-315, thereby Incorporated by Reference)

Leaf material is homogenized in 0.05 M potassium phosphate buffer (pH 6.5) and the resulting extracts are added to a disk of filter paper (Whatman No. 1). After incubation for 4-24 hours at the desired temperature (55_C.-60_C. is optimal for $T.$ $fusca$ cellulases), the reaction is stopped and reducing sugars content is determined. Alternatively, the cellulase activity on CMC is measured with a viscosity method as described by Durbin and Lewis (1988) Methods in Enzymology, 160: 314-315.

C. Expression of Cellulase Genes within the Tobacco Chloroplast

Example C1

Preparation of a Chimeric Gene Containing the $T.$ $fusca$ E5 Cellulase Coding Sequence Fused to a Modified Bacteriophage T7 Gene 10 Promoter and Terminator in Tobacco Plastid Transformation Vector pC8

Figure 2:
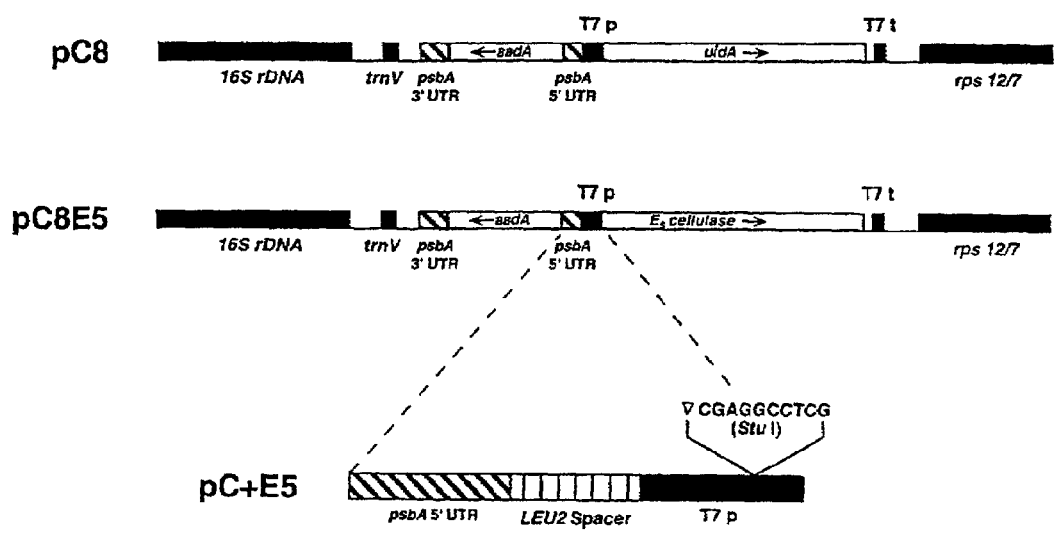
FIG. 2 depicts plastid transformation vectors described in Section C of the Examples.

Plasmid pCTE5 was digested with EcoRI, treated with Klenow DNA polymerase to fill in the recessed 3' ends, digested with NcoI and the resulting 1.5 kb DNA fragment gel purified and ligated to a 7.5 kb NcoI (cohesive end)/XbaI (filled in) DNA fragment from plastid transformation vector pC8 to create plasmid pC8E5 (FIG. 2). pC8 (Dr. Pal Maliga, Rutgers University, unpublished) is a derivative of plastid transformation vector pPRV111A (Zoubenko, O. V., Allison, L. A., Svab, Z., and Maliga, P. (1994) Nucleic Acids Res 22, 3819-3824, herein incorporated by reference in its entirety; GenBank accession number U12812) that carries a bacterial aminoglycoside-3'-adenyltransferase (aadA) gene conferring spectinomycin resistance under control of the constitutive tobacco plastid psbA gene promoter and psbA 5' and 3' untranslated RNA (UTR) sequences. The 3' end of the aadA cassette in pPRV111A is flanked by 1.8 kb of tobacco plastid DNA containing the complete trnV gene and a 5' portion of the 16S rDNA gene while the 5' end is immediately adjacent to a multiple cloning site (EcoRI, SacI, KpnI, SmaI, BamHI, XbaI, SalI, PstI, SphI, HindIII) which is in turn flanked by the 1.2 kb of plastid DNA containing the ORF 70B gene and a portion of the rps 7/12 operon. These flanking homologous regions serve to target integration of the intervening heterologous DNA into the inverted repeat region of the tobacco plastid genome at nucleotide positions 102,309 and 140,219 of the published Nicotiana tabacum plastid genome sequence (Shinozaki, K. et al. (1986) $EMBO$ $J.$ 5, 2043-2049). pC8 was obtained by cloning into the EcoRI and HindIII sites of the pPRV111A polylinker a chimeric $E.$ $coli$ uidA gene encoding β-galacturonidase (GUS) controlled by the bacteriophage T7 gene 10 promoter and terminator sequences derived from the pET21d expression vector (Novagen, Inc., Madison, Wis.).

Example C2

Preparation of a Modified Tobacco Plastid Transformation Vector Containing the $T.$ $fusca$ E5 Cellulase Coding Sequence Fused to a Modified Bacteriophage T7 Gene 10 Promoter and Terminator Engineered for Reduced Read-through Transcription Plasmid pC8 was digested with SpeI and NcoI and a 235 bp fragment containing the T7 gene 10 promoter and a portion of the divergent psbA gene promoter and 5' UTR was isolated by gel purification and cloned into the NcoI and SpeI restriction sites of vector pGEM5Zf+ (Promega, Madison Wis.) to construct plasmid pPH118. pPH118 was digested with StuI and the 3210 bp vector fragment gel purified and religated to construct plasmid pPH119 which lacks the duplicated 10 bp sequence CGAGGCCTCG (SEQ ID NO:17) (StuI site underlined) that was found by sequence analysis to be present in plasmid pC8. Elimination of the 10 bp StuI/StuI fragment in pPH119 was verified by sequencing using universal M13 forward and reverse primers.

In order to obtain a non-plastid DNA fragment to use as a spacer between the chimeric psbA/aadA selectable marker gene and the pET21d T7 gene 10 promoter in pC8, yeast shuttle vector pRS305 (Sikorski, R. S., and Hieter, P. (1989) Genetics 122, 19-27; GenBank accession number U03437) was digested with EcoRI and HincII and a 256 bp fragment of the Saccharomyces cerevisiae LEU2 gene coding sequence isolated and gel purified. Plasmid pPH119 was digested with EcoRI and DraIII and a 2645 bp fragment isolated and gel purified. pPH119 was digested with EcoRI, treated with Klenow DNA polymerase to fill in the overhanging 3' terminus, digested with DraIII and a 569 bp fragment gel purified. The three fragments were ligated to create plasmid pPH120 in which the LEU2 gene fragment is inserted between the divergent T7 gene 10 and psbA promoters of pPH119.

Plastid transformation vector pC+E5 (FIG. 2) was constructed by digesting plasmid pPH120 with NcoI/EcoRI and gel purifying a 386 bp fragment, digesting plasmid pC8E5 with NcoI/HindIII and gel purifying a 1595 bp fragment, digesting plasmid pC8 with HindIII/EcoRI and gel purifying a 7287 bp fragment, and ligating the fragments in a 3-way reaction.

Example C3

Construction of a Plastid-targeted Bacteriophage T7 RNA Polymerase Gene Fused to the Tbacco PR-1a Promoter A synthetic oligonucleotide linker comprising an NcoI restriction site and ATG start codon followed by the first seven plastid transit peptide codons from the rbcS gene (encoding the small subunit of ribulose bisphosphate carboxylase) and endogenous PstI restriction site (top strand: 5'-CAT GGC TTC CTC AGT TCT TTC CTC TGC A-3' (SEQ ID NO:18); bottom strand: 5'-GAG GAA AGA ACT GAG GAA GC-3') (SEQ ID NO:19), a 2.8 kb PstI/SacI DNA fragment of pCGN4205 (McBride, K. E. et al. (1994) PNAS 91, 7301-7305) containing the bacteriophage T7 RNA polymerase gene (T7 Pol) fused in frame to the 3' portion of the rbcS gene transit peptide coding sequence, a 0.9 kb NcoI/KpnI DNA fragment of pCIB296 containing the tobacco PR-1a promoter with an introduced NcoI restriction site at the start codon (Uknes et al. (1993) Plant Cell 5, 159 169) and 4.9 kb SfiI/KpnI and 6.6 kb SacI/SfiI fragments of binary Agrobacterium transformation vector pSGCGC1 (a derivative of pGPTV-Hyg containing the polylinker from pGEM4 (Promega, Madison Wis.) cloned into the SacI/HindIII sites) were ligated to construct pPH110.

Example C4

Biolistic Transformation of the Tobacco Plastid Genome

Seeds of Nicotiana tabacum c.v. 'Xanthi nc' were germinated seven per plate in a 1" circular array on T agar medium and bombarded in situ 12-14 days after sowing with 1 µm tungsten particles (M10, Biorad, Hercules, Calif.) coated with DNA from plasmids pC8E5 and pC+E5 essentially as described (Svab, Z. and Maliga, P. (1993) PNAS 90, 913 917). Bombarded seedlings were incubated on T medium for two days after which leaves were excised and placed abaxial side up in bright light (350-500 µmol photons/m2/s) on plates of RMOP medium (Svab, Z., Hajdukiewicz, P. and Maliga, P. (1990) PNAS 87, 8526 8530) containing 500 µg/ml spectinomycin dihydrochloride (Sigma, St. Louis, Mo.). Resistant shoots appearing underneath the bleached leaves three to eight weeks after bombardment were subcloned onto the same selective medium, allowed to form callus, and secondary shoots isolated and subcloned. Complete segregation of transformed plastid genome copies to a homoplastidic state in independent subclones was assessed by standard techniques of Southern blotting (Sambrook et al., (1989) Molecular Cloning: A Laboratory Manual, Cold Springs Harbor Laboratory, Cold Spring Harbor). BamHI/EcoRI-digested total cellular DNA (Mettler, I. J. (1987) Plant Mol Biol Reporter 5, 346-349) was separated on 1% Tris-borate (TBE) agarose gels, transferred to nylon membranes (Amersham) and probed with $^{32}$P-labeled random primed DNA sequences corresponding to a 0.7 kb BamHI/HindIII fragment from pC8 containing a portion of the rps7/12 plastid targeting sequence. Homoplastidic shoots were rooted aseptically on spectinomycin-containing MS/IBA medium (McBride, K. E. et al., (1994) PNAS 91, 7301-7305) and transferred to the greenhouse.

Example C5

Introduction of the Chimeric PR-1a/T7 Pol Gene Into the Tobacco Nuclear Genome by Agrobacterium-mediated Leaf Disc Transformation Hygromycin resistant NT-pPH110 tobacco plants were regenerated as described from shoots obtained following cocultivation of leaf disks of N. tabacum 'Xanthi' and "NahG" with GV3101 Agrobacterium carrying the pPH110 binary vector. For each transgenic line duplicate leaf punches of approximately 2-3 cm$^2$ were incubated for 2 days in 3 ml of BTH (5.6 mg/10 ml) or sterile distilled water under ca. 300 µmol/m$^2$/s irradiance. Leaf material was harvested, flash frozen and ground in liquid nitrogen. Total RNA was extracted (Verwoerd et al. (1989) NAR 17, 2362) and Northern blot analysis was carried out as described (Ward et al. (1991) The Plant Cell 3, 1085-1094) using a radiolabelled T7 RNA polymerase gene probe. Plants of nineteen NT-110X (Xanthi genetic background) and seven NT-110N (NahG genetic background) T1 lines showing a range of T7 Pol expression were transferred to the greenhouse and self pollinated. Progeny segregating 3:1 for the linked hygromycin resistance marker were selfed and homozygous T2 lines selected.

Example C6

Induction of Cellulase Expression in Plastids of Transgenic Plants

Homozygous NT-110X and NT-110N plants containing the PR-1a-T7 RNA Pol construct were used to pollinate homoplastidic Nt_pC8E5 and Nt_pC+E5 plastid transformant lines carrying the maternally inherited pC8E5 and pC+E5 cellulase constructs. The Nt_pC+E5×NT-110X or NT__110N, and Nt_pC8E5×NT-110X or NT__110N F1 progeny (which were heterozygous for the PR-1/T7 polymerase nuclear expression cassette and homoplastidic for the T7/cellulase plastid expression cassette) were germinated on soil. Upon reaching a height of 20-40 cm, the plants were sprayed with the inducer compound BTH to elicit T7 Pol-regulated expression of the E5 cellulase gene that is localized to the plastids. Plant material was harvested just prior to induction and at 8 hours and 1, 2, 3, 7, and 14 or 28 days following induction and flash frozen as described above.

Example C7

Determination of E5 Cellulase mRNA Content of Transgenic Plants

Total RNA was extracted from frozen tissue of BTH and wettable powder-sprayed control and PR-1a/7 polymerase×plastid T7/cellulase plants, and Northern blot analysis on 5 µg RNA samples was carried out as described (Ward et al. (1991) The Plant Cell 3, 1085-1094) using as a probe a radiolabelled DNA fragment containing the E5 cellulase coding sequence. Relative E5 cellulase MRNA accumulation at each time point was assessed by quantifying the radioactivity in bands hybridizing with the radiolabelled E5 cellulase probe in order to determine time courses of fold mRNA induction. The transgenic plant material of example C6 shows significant cellulase mRNA accumulation in this assay following induction, peaking at 14 days after induction. Prior to induction, no cellulase MRNA is detected.

Example C8

Determination of Cellulase Content of Transgenic Plants

In order to determine the amount of cellulase present in the tissues of transgenic plants, chemiluminescent (Amersham) Western blot analysis is performed according to the manufacturer's instructions and Harlow and Lane (1988) Antibodies: A laboratory manual, Cold Spring Harbor Laboratory, Cold Spring Harbor using antisera raised against the E5 protein and purified E5 protein standards (provided by D. Wilson, Cornell University, Ithaca, N.Y). The transgenic plant material of example C6 shows significant cellulase expression and accumulation in this assay following induction (ca. 0.3% of total soluble protein at 14 days after induction; no detectible protein prior to induction).

Example C9

Determination of Cellulase Activity in Transgenic Plants

Leaf material is harvested as described above and homogenized in PC buffer (50 mM phosphate, 12 mM citrate, pH 6.5). A standard curve (10 nanomolar to 10 micromolar) is prepared by diluting appropriate amounts of 4-methylumbelliferone (MU, Sigma Cat. No. M1381) in PC buffer. Duplicate 100 µl aliquots of each standard and duplicate 50 µl aliquots of each sample are distributed to separate wells of a 96-well microtiter plate. 50 µl of 2 mM 4-methylumbelliferyl-b-D-cellobiopyranoside (MUC, Sigma Cat. No. M6018) prepared in PC buffer is then added to each sample well and the plate is sealed to prevent evaporation and incubated for 30 minutes at 55° C. or at other temperatures ranging from 37° C. to 65° C. The reaction is stopped by adding 100 µl of 0.15 M glycine/NaOH (pH 10.3) and the fluorescence emission at 460 nm measured with a microplate fluorometer (excitation wavelength=355 nm).

Example C10

Induction of GUS Expression in Plastids of Transgenic Plants

The N. tabacum 'Xanthi' plastid transformant line 4276P described by McBride et al. ((1994) PNAS 91: 7301-7305) was pollinated by homozygous NT-110X6b-5 plants containing the PR-1a/T7 RNA polymerase. 4276P differs from pC8 only with respect to (a) the promoter used to express the aadA selectable marker (which has the 16S ribosomal RNA gene promoter rather than the psbA gene promoter used in pC8), (b) the presence of a psbA gene 3' untranslated region between the GUS gene and the T7 terminator, and (c) the absence of a lac operator and duplicated StuI restriction site sequence in the T7 promoter. F1 plants from this cross heterozygous for the PR-1a/T7 polymerase nuclear expression cassette and homoplastidic for the T7/GUS plastid expression cassette were germinated in soil. Upon reaching a height of 20 to 40 cm the plants were sprayed with either an inert wettable powder suspension or a formulation of the inducer compound BTH with wettable powder. Control untransforned N. tabacum 'Xanthi', NT-110X6b-5, and 4276P plants germinated in soil at the same time were sprayed in a similar manner. Plant material (one leaf from each of three independent plants of each genotype) was harvested just prior to spraying and at 8 hours and 1, 2, 3, 7, and 28 days following spraying, and flash frozen as described above.

Example C11

Determination of GUS MRNA Content of Transgenic Plants

Total RNA was extracted from frozen tissue of BTH and wettable powder-sprayed control and PR-1a/T7 polymerase×plastid T7/GUS plants, and Northern blot analysis on 5 µg RNA samples was carried out as described (Ward et al. (1991) The Plant Cell 3, 1085-1094) using as a probe a 500 bp radiolabelled 5' fragment of the GUS gene. GUS mRNA accumulation at each time point was assessed by quantifying the radioactivity in bands hybridizing with the radiolabelled GUS probe, as well as by scanning the ethidium-bromide fluorescence present in the prominent RNA band which became visible starting at the 3 day post-spray time point and which was observed to co-migrate with the hybridizing GUS RNA band on Northern blots. Chemically inducible GUS RNA in the plastid was observed to reach a peak level of 14% of total ethidium-stainable RNA (this includes all RNA species present in the plant, including the non-protein coding ribosomal RNA which makes up a majority of the stainable plant RNA) between 7 and 28 days after induction with BTH (see Table 1) and is much higher (over 1000-fold) than the peak chemically inducible GUS mRNA accumulation for nuclear PR- I a/GUS transformants.

Example C12

Determination of GUS Protein Content of Transgenic Plants

In order to determine the amount of GUS present in the tissues of transgenic plants, chemiluminescent (Amersham) Western blot analysis was performed according to the manufacturer's instructions and Harlow and Lane (1988) Antibodies: A laboratory manual, Cold Spring Harbor Laboratory, Cold Spring Harbor, using GUS antisera purchased from Molecular Probes and purified GUS protein standards (Sigma). Proteins from frozen, ground leaf material harvested as above were solubilized by extraction in 50 mM Tris pH 8.0, 1 mM EDTA, 1 mM PTT, 1 mM AEBSP, and 1 mM DTT and 5 to 25 µg protein run on each lane of 10% polyacrylamide gels. GUS protein accumulation in the plastid transformed plants is sustained over 7-28 days and beyond, and is extraordinarily high (much higher than peak GUS accumulation for nuclear PR-1a/GUS), exceeding 20% of of total protein by 28 days. By comparison, GUS protein accumulation in the nuclear PR1a/GUS transformants peaks somewhat earlier (about 3 days from induction, rather than 7-28 days) and the protein accumulation is not sustained, but declines to the limits of detection by 28 days.

Example C13

Determination of GUS Activity in Transgenic Plants

Frozen leaf tissue was ground in a mortar with a pestle in the presence of liquid nitrogen to produce a fine powder. Leaf extracts were prepared in GUS extraction buffer (50 mM sodium phosphate pH7.0, 0.1% Triton-X 100, 0.1% sarkosyl, 10 mM beta-mercaptoethanol) as described by Jefferson, R. A. et al. (1986), PNAS USA 83, 8447-8451. The reactions were carried out in the wells of opaque microtiter plates by mixing 10 ul of extract with 65 ul of GUS assay buffer (50 mM sodium phosphate pH 7.0, 10 mM EDTA, 0.1% Triton X-100, 10 mM beta-mercaptoethanol) containing 4-methyl umbelliferyl glucuronide (MU) at a final concentration of 2 mM in a total volume of 75 ul. The plate was incubated at 37° C. for 30 minutes and the reaction was stopped by the addition of 225 ul of 0.2 M sodium carbonate. The concentration of fluorescent indicator released was determined by reading the plate on a Flow Labs Fluoroskan II ELISA plate reader. Duplicate fluorescence values for each sample were averaged, and background fluorescence (reaction without MUG) was subtracted to obtain the concentration of MU for each sample. The amount of protein in each extract was determined using the bicinchoninic acid technique (BCA, Pierce Biochemicals) according to the manufacturer's recommendations except that protein extracts were pretreated with iodacetamide (Sigma) to eliminate background signal caused by the reductant (beta-mercaptoethanol) present in the extraction buffer. The specific activity was determined for each sample and was expressed in pmoles MU/mg protein/minute. For each tissue sample assayed from a particular time point following BTH application, the specific activity of the BTH-induced sample was divided by the specific activity of the pre-BTH treatment control sample, thus yielding the induction of GUS expression. (See Table 1)

TABLE I pPH110X6b × 4276P: Induction of GUS RNA and GUS Activity by Spraying with BTH

| Days + BTH | GUS activity (pmol MU/mg/min) | Fold Induction (GUS activity) | % Total RNA | Fold Induction (GUS RNA) |
|---|---|---|---|---|
| 0.0 | 598 | 1 | <0.013 | 1 |
| 0.3 | 434 | 0.7 | <0.013 | 24 |
| 1.0 | 14,516 | 24 | 0.108 | 959 |
| 2.0 | 230,031 | 380 | 0.873 | 1,897 |
| 3.0 | 456,486 | 749 | 2.663 | 2,396 |
| 7.0 | 2,424,725 | 3,999 | 7.745 | 2,875 |
| 28.0 | 1,922,466 | 3,106 | 24.596 | 3,392 |

What is claimed is:

1. A transgenic plant comprising a nucleic acid encoding a microbial β-1,4-endoglucanase (EC 3.2.1.4), wherein said nucleic acid is stably integrated into the nuclear genome of a cell of the plant and is under the control of a promoter active in a plant, wherein the promoter is an inducible promoter.

2. The transgenic plant of claim 1, wherein the microbial β1,4-endoglucanase is thermostable.

3. The transgenic plant of claim 1, wherein the microbial β-1,4-endoglucanase is from a cellulolytic bacterium.

4. The transgenic plant of claim 1, wherein the microbial β-1,4-endoglucanase is from a filamentous fungus.

5. The transgenic plant of claim 1, wherein the promoter is a wound inducible promoter.

6. The transgenic plant of claim 1, wherein the promoter is a chemically-inducible promoter.

7. A transgenic plant comprising a nucleic acid encoding a microbial β-1,4-endoglucanase (EC 3.2.1.4), wherein said nucleic acid is stably integrated into the nuclear genome of a cell of the plant and is under the control of a promoter active in a plant, wherein the promoter is a wound inducible or a chemically-inducible promoter.

8. A transgenic seed comprising a nucleic acid encoding a microbial β-1,4-endoglucanase (EC 3.2.1.4), wherein said nucleic acid is stably integrated into the nuclear genome of a cell of the seed and is under the control of a promoter active in a plant, wherein the promoter is an inducible promoter.

9. A transgenic plant comprising a nucleic acid encoding a microbial β-1,4-endoglucanase (EC 3.2.1.4) and a targeting sequence, wherein the nucleic acid is stably integrated into the nuclear genome of a cell of the plant and is under control of a promoter active in a plant and wherein the targeting sequence targets the microbial β-1,4-endoglucanase to a compartment selected from the group consisting of vacuole, chloroplast, mitochondria, peroxisome, apoplast, and ER.

10. The transgenic plant of claim 9, wherein the promoter determines a spatial or temporal expression pattern for the microbial β-1,4-endoglucanase.

11. The transgenic plant of claim 9, wherein the promoter is an inducible promoter.

12. The transgenic plant of claim 11, wherein the promoter is a wound inducible promoter.

13. The transgenic plant of claim 11, wherein the promoter is a chemically-inducible promoter.

14. The transgenic plant of claim 9, wherein the microbial β1,4-endoglucanase is thermostable.

15. The transgenic plant of claim 9, wherein the microbial β-1,4-endoglucanase is from a cellulolytic bacterium.

16. The transgenic plant of claim 9, wherein the microbial β-1,4-endoglucanase is from a filamentous fungus.

17. A transgenic seed comprising a nucleic acid encoding a microbial β-1,4-endoglucanase (EC 3.2.1.4) and a targeting sequence, wherein the nucleic acid is stably integrated into the nuclear genome of a cell of the seed and is under control of a promoter active in a plant and wherein the targeting sequence targets the microbial β-1,4-endoglucanase to a compartment selected from the group consisting of vacuole, chloroplast, mitochondria, peroxisome, apoplast, and ER.

18. A transgenic plant comprising a nucleic acid encoding a microbial β-1,4-endoglucanase (EC 3.2.1.4), wherein the nucleic acid is stably integrated into a plastid genome of the plant and is under control of an inducible promoter.

19. The transgenic plant of claim 18, wherein the microbial β-1,4-endoglucanase is from a cellulolytic bacterium.

20. The transgenic plant of claim 18, wherein the microbial β-1,4-endoglucanase is from a filamentous fungus.

21. The transgenic plant of claim 18, wherein the promoter is a chemically inducible promoter.

22. The transgenic plant of claim 18, wherein the promoter is a wound inducible promoter.

23. The transgenic plant of claim 18, wherein the microbial β-1,4-endoglucanase is thermostable.

24. A transgenic seed comprising a nucleic acid encoding a microbial β-1,4-endoglucanase (EC 3.2.1.4), wherein the nucleic acid is stably integrated into a plastid genome of the plant and is under control of an inducible promoter.

25. A transgenic plant comprising a nucleic acid encoding a microbial β-1,4-endoglucanase (EC 3.2.1.4) from a *Thermomonospora* bacterium, wherein said nucleic acid is stably integrated into the nuclear genome of a cell of the plant and is under the control of a promoter active in a plant, wherein the promoter is an inducible promoter.

26. The transgenic plant of claim 25, where in the microbial β-1,4-endoglucanase is from *T. fusca*.

27. A transgenic plant comprising a nucleic acid encoding a microbial β-1,4-endoglucanase (EC 3.2.1.4) is from a *Thermomonospora* bacterium, wherein the nucleic acid is stably integrated into a plastid genome of the plant and is under control of an inducible promoter.

28. The transgenic plant of claim 27, wherein the microbial β1,4-endoglucanase is from *T. fusca*.

* * * * *

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Consensus tranlation (xi) SEQUENCE DESCRIPTION: SEQ ID NO: 1:

GTCGACCATG GTC                                                        13

(2) INFORMATION FOR SEQ ID NO: 2:

(i) SEQUENCE CHARACTERISTICS:
      (A) LENGTH: 12 base pairs
      (B) TYPE: nucleic acid

```
        (C) STRANDEDNESS: single
        (D) TOPOLOGY: linear (ii) MOLECULE TYPE: other nucleic acid
        (A) DESCRIPTION: /desc = "Consensus translation (xi) SEQUENCE DESCRIPTION: SEQ ID NO: 2:

TAAACAATGG CT                                                              12

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Molecular adaptor used to (xi) SEQUENCE DESCRIPTION: SEQ ID NO: 3:

AATTCTAAAG CATGCCGATC GG                                                   22

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Molecular adaptor used to (xi) SEQUENCE DESCRIPTION: SEQ ID NO: 4:

AATTCCGATC GGCATGCTTT A                                                    21

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Molecular adaptor used in (xi) SEQUENCE DESCRIPTION: SEQ ID NO: 5:

AATTCTAAAC CATGGCGATC GG                                                   22

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Molecular adaptor used in (xi) SEQUENCE DESCRIPTION: SEQ ID NO: 6:

AATTCCGATC GCCATGGTTT A                                                    21
```

(2) INFORMATION FOR SEQ ID NO: 7:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Molecular adaptor sequence (xi) SEQUENCE DESCRIPTION: SEQ ID NO: 7:

CCAGCTGGAA TTCCG                                                    15

(2) INFORMATION FOR SEQ ID NO: 8:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Molecular adaptor sequence (xi) SEQUENCE DESCRIPTION: SEQ ID NO: 8:

CGGAATTCCA GCTGGCATG                                                19

(2) INFORMATION FOR SEQ ID NO: 9:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Primer E11"

(xi) SEQUENCE DESCRIPTION: SEQ ID NO: 9:

GCGCCCATGG ACGAAGTCAA CCAGATTCGC                                    30

(2) INFORMATION FOR SEQ ID NO: 10:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Primer E12"

(xi) SEQUENCE DESCRIPTION: SEQ ID NO: 10:

CCAGTCGACG TTGGAGGTGA AGAC                                          24

(2) INFORMATION FOR SEQ ID NO: 11:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Primer E21"

(xi) SEQUENCE DESCRIPTION: SEQ ID NO: 11:

GCGCGCCATG GCCAATGATT CTCCGTTCTA C                                  31

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer E22"

(xi) SEQUENCE DESCRIPTION: SEQ ID NO: 12:

GGGACGGTTC TTCAGTCCGG CAGC                       24

(2) INFORMATION FOR SEQ ID NO: 13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer E51"

(xi) SEQUENCE DESCRIPTION: SEQ ID NO: 13:

CGCCCATGGC CGGTCTCACC GCCACAGTC                  29

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer E52"

(xi) SEQUENCE DESCRIPTION: SEQ ID NO: 14:

GACGACCTCC CACTGGGAGA CGGTG                      25

(2) INFORMATION FOR SEQ ID NO: 15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer VAC1"

(xi) SEQUENCE DESCRIPTION: SEQ ID NO: 15:

CATGCCATGG GTGAGGCCTC CGAGCTGTTC C                31

(2) INFORMATION FOR SEQ ID NO: 16:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer VAC2"

(xi) SEQUENCE DESCRIPTION: SEQ ID NO: 16:

TGCGAGCTCT TACATAGTAT CGACTAAAAG TCCGGACTGG AGCTTGCTCC GCAC      54

-continued (2) INFORMATION FOR SEQ ID NO: 17:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Sequence present in plasmid (xi) SEQUENCE DESCRIPTION: SEQ ID NO: 17:

```
CGAGGCCTCG                                                          10
```

(2) INFORMATION FOR SEQ ID NO: 18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Top strand of (xi) SEQUENCE DESCRIPTION: SEQ ID NO: 18:

```
CATGGCTTCC TCAGTTCTTT CCTCTGCA                                      28
```

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Bottom strand of (xi) SEQUENCE DESCRIPTION: SEQ ID NO: 19:

```
GAGGAAAGAA CTGAGGAAGC                                               20
```